US008383601B2

(12) United States Patent
Koch et al.

(10) Patent No.: US 8,383,601 B2
(45) Date of Patent: Feb. 26, 2013

(54) TISSUE SPECIFIC GENE THERAPY TREATMENT

(75) Inventors: Walter J. Koch, Broomall, PA (US); Patrick Most, Philadelphia, PA (US); Sven T. Pleger, Heidelberg (DE); Joseph E. Rabinowitz, Elkins Park, PA (US)

(73) Assignee: Thomas Jefferson University, Philadelphia, PA (US)

( * ) Notice: Subject to any disclaimer, the term of this patent is extended or adjusted under 35 U.S.C. 154(b) by 250 days.

(21) Appl. No.: 12/447,558

(22) PCT Filed: Oct. 30, 2007

(86) PCT No.: PCT/US2007/022861

§ 371 (c)(1), (2), (4) Date: Jan. 25, 2010

(87) PCT Pub. No.: WO2008/054713

PCT Pub. Date: May 8, 2008

(65) Prior Publication Data

US 2010/0190840 A1 Jul. 29, 2010

Related U.S. Application Data

(60) Provisional application No. 60/855,331, filed on Oct. 30, 2006.

(51) Int. Cl.

*A61K 48/00* (2006.01)
*C12N 15/11* (2006.01)
*C12N 5/00* (2006.01)

(52) U.S. Cl. .......................... 514/44; 536/23.1; 435/325

(58) Field of Classification Search .................... 514/44; 536/23.1; 435/325

See application file for complete search history.

(56) References Cited

U.S. PATENT DOCUMENTS

2002/0022259 A1 2/2002 Lee et al.
2002/0100069 A1* 7/2002 Olson ............................... 800/8
2003/0100526 A1 5/2003 Souza et al.
2004/0180440 A1 9/2004 Zolotukhin
2005/0233329 A1* 10/2005 McSwiggen et al. ............. 435/6
2006/0018841 A1 1/2006 Arbetman et al.
2006/0188484 A1 8/2006 Rabinowitz et al.

OTHER PUBLICATIONS

Bischoff et al (Genomics, 68: 63-70, 2000).*

Lemonnier, M. et al., Journal of Biological Chemistry, 279(53): 55651-55658 (2004). "Characterization of a cardiac-specific enhance, which directs alpha-cardiac actin gene transcription in the mouse adult heart."

Most, P. et al., Journal of Clinical Investigation, 114(11):1550-1563 (2004). "Cardiac adenoviral S100A1 gene delivery rescues failing myocardium."

Pleger, S.T. et al., Molecular Therapy, 12(6):1120-1129 (2005). "S100A1 Gene Therapy Preserves in Vivo Cardiac Function after Myocardial Infarction."

Pleger, S.T. et al., Circulation, 114(18) Suppl. S: 49 (2006). "Long-term cardioselective S100A1 gene therapy improves cardiac function in heart failure."

Pleger, S.T. et al., Circulation, 115(19):2506-2515 (2007). "Stable myocardial-specific AAV6-S100A1 gene therapy results in chronic functional heart failure rescue."

Du et al., Mol Cell Biol, 22:2821-2829 (2002). "Impaired cardiac contractility response to hemodynamic stress in S100A1-deficient mice."

Kettlewell et al., J Mol Cell Cardiol, 39:900-910 (2005). "S100A1 increases the gain of excitation-contraction coupling in isolated rabbit ventricular cardiomyocytes."

Remppis et al., J Gene Med, 6:387-394 (2004). "S100A1 gene transfer: a strategy to strengthen engineered cardiac grafts."

* cited by examiner

*Primary Examiner* — Gerald Leffers, Jr.
*Assistant Examiner* — Magdalene Sgagias
(74) *Attorney, Agent, or Firm* — David S. Resnick; Tari W. Mills; Nixon Peabody LLP

(57) ABSTRACT

The invention provides nucleic acid segments, compositions and methods for the treatment of heart failure, vascular dysfunction, endothelial dysfunction, diabetes, $[Ca^{2+}]i$ regulation and NO synthase dysfunction. Adeno-associated and adenovirus are used as gene delivery vectors for the nucleic acid segments to product long term over-expression of S100A1, a small calcium sensing protein associated with the disclosed ailments and dysfunctions.

18 Claims, 15 Drawing Sheets a
EF (%)
b
EF (%)
c
% change of EF
d
LVIDd (mm)
e
LVIDd (mm)
f
AWTs (mm)
Sham
HF/Saline
HF/GFP
HF/S100A1
HF/GFP meto
HF/S100A1 meto a
10000
5000
0
-5000
-10000
Sham
HF/Saline
HF/GFP
HF/S100A1
HF/GFP meto
HF/S100A1 meto
c
Sham
HF/Saline
HF/GFP
HF/S100A1
HF/GFP meto
HF/S100A1 meto a
relative S100A1 mRNA expression levels
0
1
2
3
b
relative SERCA2a mRNA expression levels
c
relative PLB mRNA expression levels
0
0.2
0.4
0.6
0.8
1.0
1.2
d
relative ANF mRNA expression levels
0
5
10
15
20
e
relative TGFβ1 mRNA expression levels
f
relative Collagen I mRNA expression levels
0
1
2
3
4
5
6
Sham
HF/Saline
HF/GFP
HF/S100A1
HF/GFP meto
HF/S100A1 meto

&
*

A
% of PE
120
80
40
0
10-9 10-8 10-7 10-6 10-5 (M)
Acetylcholine
B
% of PE
120
80
40
0
10-10 10-9 10-8 10-7 10-6 10-5 (M)
SNP
C
% of PE
120
80
40
0
10-9 10-8 10-7 10-6 10-5 (M)
Acetylcholine
D
% of PE
120
80
40
0
10-10 10-9 10-8 10-7 10-6 10-5 (M)
SNP A
B
WT
SKO
Blood Pressure (mmHg)
180
160
140
120
100
80
1 sec
C
D
E
F
SBP (mmHg)
DBP (mmHg)
MBP (mmHg)
Heart rate (per min)
WT
SKO
*

A
NO (nM)/mg tissue
1000
800
600
400
200
0
WT
SKO
*
B
NO amplitude (nM)/mg tissue
in response to Ach
500
400
300
200
100
0
WT
SKO
*
C
S100A1
eNOS
Hsp 90
Actin
WT
SKO A
340/380 nm ratio
1.6
1.4
1.2
1.0
0.8
0
100
200
300
sec
WT
SKO
B
$Ca^{2+}$ amplitude
(340/380 nm ratio)
0.4
0.3
0.2
0.1
0
WT
SKO
SKO AdGFP
SKO AdS100A1
*
*

Figure 13

ITR
ITR
CMV
GFP
SV40 pA+
Tie2 enhancer*
EF1α promoter
S100A1 transgene

SEQUENCE LISTING

<160> NUMBER OF SEQ ID NOS: 30

<210> SEQ ID NO 1
<211> LENGTH: 319
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
aggaattcta aatttacgtc tgcttcctgt caatgggcat cctcactgtc aaatgcagat     60

ggtacagcag ggcttggtct cagccaggca ggcctctccc cagtctccat ggctcagctg    120

tccagcagtt tcatccctag accatcccaa acatggttga gaagctctga ggggaggacc    180

cagcactgcc cggcccctga agtatctaat cagcagtcct gctcagcata tcaatccaag    240

cccactctag acagagatgc cggtgcccag ttttctattt ttaactggtg tgaactgaag    300

gaaaaagcag ctgactagt                                                 319
```

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Synthetic consensus sequence

<400> SEQUENCE: 2

```
cagctg                                                                 6
```

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3

```
ctaaaaatag                                                            10
```

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4

```
ctatttttag                                                            10
```

<210> SEQ ID NO 5
<211> LENGTH: 694
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
ccggccggcc gttgctgaaa accctggatc ccttgggggg caaatgctgc ctccagttgc     60

tgcctctatg cctcaggttt gatttgcacc tcttgtgtga gggcatgggg attgtggggg    120
```

```
attgtggggg cactggacac cactcaggct gggaatgttc cctggagagg gggggtggga    180

ccctgtcccg tgcagggcca aatcctgacg tatgcatgct tcacctttta attggagaaa    240

agcccttctg tttgagtctg ggataaaatg aacggcatct cttcccatcc ctgccctgtg    300

gaggccaggg agccggttgt ggtggaaatg tcttaaaggg ggtcagttga agtgttttta    360

cttttgtgtg tggtgcacag ggtaacccct tcatgaggac acaccgtctc ttgatcactg    420

atatttatgc atacacgtac acactggggc aagagtgggg ggggtcactt catggaccct    480

ccccacacac acacacctca gtggaggcga gcatcagcgt ttacccgagc cgctgtcaat    540

cgtatgcgcc tgtgcagtgg ttggcagtgg gggtcgggaa tggggtgggc tgtacacttt    600

tgcagattgt gtctttcccc gccatcggcc tagctggctg actaccctgc cctccggccg    660

tggcacccca tcacaccctg tgtttgtctc ccag                                694


<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

ccggccggcc g                                                          11


<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

gaggggggt                                                             10


<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

gtgggggggt                                                            10


<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

aggaattcta aatttacgtc tgcttcctgt caatgggc                             38


<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
```

primer

<400> SEQUENCE: 10
ccagactagt cagctgcttt tccttcagtt cacaccag 38

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ctgccatggg ctctgagctg gagacggcg 29

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
ccagctagct cattcaactg ttctccccag aagaaatt 38

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tgccggtaga agatgaggtc 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tgcttttcaa gagggcagat 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tgagacgctc aagtttgtgg 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 16

atgcagaggg ctggtagatg                                                20


<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

tacctcactc gctcggctat                                                20


<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

gatgcagatc agcagcagac                                                20


<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

cgatggagac cctcatcaac                                                20


<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

tggaagtcca cctccccgtc                                                20


<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

ggcacaggtg ttgagccctt tcca                                           24


<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
```

caggtgttga gccctttcca 20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ccagttcgag tatggaagcg a 21

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
aggtgatgtt ctggg 15

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ccctctcacc atctctgagc 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
cggttgggga acaagtagaa 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tcaagaacga aagtcggagg 20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ggacatctaa gggcatcac 19

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29 ctawwwwtag 10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30 gwgggggggt 10

TISSUE SPECIFIC GENE THERAPY TREATMENT

CROSS-REFERENCE TO RELATED APPLICATION

This application is a 35 U. S. C. §371 National Phase Entry of the co-pending International Application No. PCT/US2007/022861 filed on Oct. 30, 2007, which designates the United States, and claims the benefit under 35 U. S. C. §119 (e) of U.S. provisional patent application No. 60/855,331 filed Oct. 30, 2006, the contents of which are incorporated herein by reference in its entirety.

GOVERNMENT SUPPORT

This invention was made with Government support under Grant No.: R01 HL56205 and P01 HL075443-project 2 awarded by the National Institutes of Health. The Government has certain rights in the invention.

BACKGROUND OF THE INVENTION

Cardiovascular disease remains a leading cause of mortality in the developed world[1,2]. In particular, chronic heart failure (HF) continues to represent an enormous clinical challenge since HF mortality and incidence continue to rise[2,3]. Although pharmacological therapy has considerably improved HF care over the last two decades, existing treatments are not ideal since they often fail to support myocardium and increase global cardiac function[1-3]. Therefore, novel therapeutic approaches to target the underlying molecular defects of ventricular dysfunction in HF are needed. One hallmark molecular defect in failing myocardium is dysfunctional intracellular calcium ($Ca^{2+}$) handling and several $Ca^{2+}$-cycling proteins have been identified as potential targets for reversing failing myocyte function[4,5].

S100A1 is a low molecular weight (~10 kDa) $Ca^{2+}$-sensing protein of the EF-hand type known to modulate intracellular calcium $[Ca^{2+}]_i$-handling in various cell types such as neurons, skeletal muscle and cardiomyocytes.[7,14,38-39] Several biological activities such as the regulation of myocardial- and skeletal muscle contractility, cytoskeleton-mediated interactions, apoptosis, regulation of metabolic enzymes, proliferation and cell differentiation are affected by S100A1 mediated alterations in $[Ca^{2+}]_i$.[40-42] S100A1 is especially interesting with respect to cardiovascular diseases since cardiac S100A1 expression levels are significantly down-regulated in end-stage heart failure (HF). S100A1 is a positive inotropic regulator of myocardial function in vitro and in vivo[6-10]. This effect is mainly mediated by a significant gain in sarcoplasmic reticulum (SR) $Ca^{2+}$-cycling.[13,14] Consistent with S100A1 being a key player in cardiac contractile function, data generated from S100A1 knock-out mice demonstrate that the loss of S100A1 expression leads to an inability of the heart to adapt to acute or chronic hemodynamic stress in vivo[11,12]. Importantly, S100A1 mediated affects on cardiac contractile function do not interfere with basic regulatory mechanisms of myocardial contractility[9] and have been found to be independent of β-adrenergic signaling[7]. Functional properties of S100A1 in cardiomyocytes are mainly caused by increased sarcoplasmic reticulum (SR) $Ca^{2+}$-ATPase (SERCA2a) activity, diminished diastolic SR $Ca^{2+}$-leak and augmented systolic open probability of the ryanodine receptor (RyR) causing an overall significant gain in SR $Ca^{2+}$-cycling[13-15]. This demonstrates a potential distinct mechanism of action for S100A1 altering $Ca^{2+}$-handling in both phases of SR function.

Recently S100A1 expression has been described in endothelial cells (EC).[43] EC synthesize and release vasoactive mediators in response to neurohumoural and physical stimuli, thus playing an important role in the regulation of vascular function. A well characterized and critical regulator of endothelial function is nitric oxide (NO) which is generated by endothelial NO synthase (eNOS or NOS3).[44] Importantly, activation of eNOS is classically dependent on increased $[Ca^{2+}]_i$ which can be induced by agonists such as acetylcholine (ACh) or bradykinin.[45,46] NO contributes to endothelium-dependent vascular relaxation and has additional functional roles such as anti-leukocyte adhesion, anti-proliferative and anti-apoptotic effects on the vascular wall.[45,47] Loss of endothelial NO results in endothelial dysfunction which occurs in a variety of cardiovascular diseases and is associated with adverse effects such as vascular inflammation, impaired vascular function and long-term vascular remodeling.[48] Moreover, recent data provide evidence that endothelial dysfunction in HF is also associated with an increased mortality risk in patients with both ischemic and non-ischemic HF.[49]

Since S100A1 play a significant role of in the regulation of $[Ca^{2+}]_i$-transients in various cell types[7, 14, 38-39], and it being highly and preferentially expressed in the healthy heart while it is found to be significantly down-regulated in HF[16], it would appear that S100A1 is important in HF. Accordingly, a method of chronic S100A1 gene delivery to failing myocardium can be used to improve SR $Ca^{2+}$-signaling and to support contractile function in HF. However, before this potential target as well as others for HF gene therapy are realized[17], safe, efficient and reproducible gene therapy vector systems must be established and tested. It is becoming increasingly clear that recombinant adeno-associated viral (rAAV) vectors have properties amenable to future human use and S100A1 delivered to myocardium using these vectors may indeed fulfill the currently unmet promise of HF gene therapy.

SUMMARY OF THE INVENTION

The expression of the small $Ca^{2+}$-sensing protein S100A1 is abnormal in heart failure and several disease states such as vascular dysfunction, hypertension, endothelial dysfunction, and diabetes. Chronic over-expression of S100A in the heart muscles and in the tissue types associated with the various disease states can help alleviate heart failure and the various disease states.

Accordingly, embodiments of the present invention provide a cardiac tissue-specific nucleic acid segment comprising: (a) a first regulatory sequence comprising a cardiac specific enhancer sequence; (b) a second regulatory sequence comprising a promoter sequence; and (c) a multiple restriction site for insertion of a target nucleic acid operatively linked to the second regulatory sequence. The cardiac specific enhancer sequence comprises a nucleotide sequence corresponding to the proximal enhancer region of the α cardiac actin gene containing one or more MEF2 sequences. In one embodiment, the cardiac specific enhancer sequence further comprises a repressor sequence. In another embodiment, the cardiac specific enhancer sequence further comprises one or more enhancer MyoD consensus sequences. The promoter sequence comprises an EF1 α promoter sequence. The target nucleic acid is selected from the group consisting of S100A1, SERCA, FK506BP 12.6, phospholamban, inhibitory RNAs for NKX, GRK2, GRK5, and the carboxyl terminal fragment of GRK2 (βARKct).

In a preferred embodiment, the cardiac specific enhancer sequence comprises the sequence AGGAATTCTAAATT-TACGTCTGCTTCCTGTCAATGGGCATC-CTCACTGTCAAATGCA GATGGTACAGCAGGGCTTG-GTCTCAGCCAGGCAGGCCTCTCCCCAGTCTCCATGGCT CAGCTGTCCAGCAGTTTCATCCCTAGAC-CATCCCAAACATGGTTGAGAAGCTCTGAG GGGAG-GACCCAGCACTGCCCGGCCCCTGAAG-TATCTAATCAGCAGTCCTGCTCAGC ATATCAATCCAAGCCCACTCTAGACA-GAGATGCCGGTGCCCAGTTTTCTATTTTTAA CTGGT-GTGAACTGAAGGAAAAAGCAGCTGACTAGT (SEQ. ID. No. 1) and can include Myo D consensus sequence CAGCTG (SEQ. ID. No. 2) or an MEF2 sequence CTA(A/T)$_4$TAG (SEQ. ID. No. 3 or 4).

In one embodiment, the cardiac tissue-specific nucleic acid segment further comprising a third regulatory sequence comprising a cardiac specific enhancer sequence and a fourth regulatory sequence comprising a promoter sequence and a second multiple restriction site for insertion of a target nucleic acid operatively linked to the fourth regulatory sequence. This cardiac specific enhancer sequence further comprises a repressor sequence.

In another embodiment, the invention provides an endothelial cell-specific nucleic acid segment comprising: (a) a first regulatory sequence comprising a endothelial cell specific enhancer sequence; (b) a second regulatory sequence comprising a promoter sequence; and (c) a multiple restriction site for insertion of a target nucleic acid operatively linked to the second regulatory sequence. The endothelial cell specific enhancer sequence comprises a nucleotide sequence corresponding to Tie2 enhancer domain and can also further comprises a repressor sequence. The promoter sequence comprises an EF1α promoter sequence. The endothelial cell-specific nucleic acid segment described herein, wherein the target nucleic acid is selected from the group consisting of S100A1, SERCA2b, SERCA3, eNOS, and nNOS.

In one embodiment, the endothelial cell-specific nucleic acid segment further comprises a third regulatory sequence comprising a endothelial cell enhancer sequence and a fourth regulatory sequence comprising a promoter sequence and a second multiple restriction site for insertion of a target nucleic acid operatively linked to the fourth regulatory sequence.

In one embodiment, the invention provides a cardiac tissue-specific nucleic acid segment or an endothelial cell-specific nucleic acid segment as disclosed herein, further comprising a gene delivery vector. The gene delivery vector function to transport or transfer the nucleic acid segment of the invention into target cells, for example, the cardiac cells and the endothelial cells. The gene delivery vector is selected from the group consisting of an adeno-associated virus, an adenovirus, a lentivirus, a retrovirus, a naked DNA, and a liposome. In a preferred embodiment, the cardiac-specific nucleic acid gene delivery vector is a recombinant adeno-associated virus vector, a rAAV6. In a preferred embodiment, the endothelial cell-specific nucleic acid segment gene delivery vector is an adenovirus.

In one embodiment, the enhancer or promoter sequences of the cardiac specific nucleic acid segment or the endothelial cell-specific nucleic acid segment are selected from the group consisting of the enhancer and promoter segments of the Pleiotropin (GenBank accession AL56812 and BC005916), Pleckstrin homology-like domain (AA576961), Collagen type XXIα1 (NM_030820), Cyclin G2 (AW134535), Ligatin (NM_006893), FK506 bp 12.6, SOD2, SOD3, and phospholamban genes.

In one embodiment, the invention provides a method of treating heart failure comprising administering to a subject in need thereof a therapeutically effective amount of the nucleic acid segment described herein. The method further comprise administering a therapeutically effective amount of a β-blocker such as alprenolol, atenolol, and butaxamine.

In one embodiment, the invention provides a method of treating heart failure comprising administering to a subject in need thereof a therapeutically effective amount of the nucleic acid segment wherein the target nucleic acid is S100A1. The method further comprise administering a therapeutically effective amount of a β-blocker such as alprenolol, atenolol, and butaxamine.

In one embodiment, a method of treating vascular dysfunction comprising administering to a subject in need thereof a therapeutically effective amount of the nucleic acid segment described herein is provided.

In one embodiment, a method of treating vascular dysfunction comprising administering to a subject in need thereof a therapeutically effective amount of the nucleic acid segment described herein wherein the target nucleic acid is S100A1, is provided.

In one embodiment, a method of treating hypertension comprising administering to a subject in need thereof a therapeutically effective amount of the nucleic acid segment described herein is provided.

In one embodiment, a method of treating hypertension comprising administering to a subject in need thereof a therapeutically effective amount of the nucleic acid segment described herein, wherein the target nucleic acid is S100A1, is provided.

In one embodiment, a method of treating endothelial dysfunction comprising administering to a subject in need thereof a therapeutically effective amount of the nucleic acid segment described herein is provided.

In one embodiment, a method of treating endothelial dysfunction comprising administering to a subject in need thereof a therapeutically effective amount of the nucleic acid segment described herein, wherein the target nucleic acid is S100A1, is provided.

In one embodiment, a method of modulating $[Ca^{2+}]_i$ comprising administering a therapeutically effective amount of the nucleic acid segment, wherein the target nucleic acid is S100A1, is provided.

In one embodiment, a method of modulating endothelial NO synthase (eNOS or NOS3) comprising administering a therapeutically effective amount of the nucleic acid segment, wherein the target nucleic acid is S100A1, is provided.

In one embodiment, a method of treating diabetes comprising administering to a subject in need thereof a therapeutically effective amount of the nucleic acid segment described herein is provided.

DESCRIPTION OF THE DRAWINGS

FIG. 6 S100A1 is expressed in EC. Representative western blot of RCEC reveals adenovirally over-expressed S100A1 (positive control) (1) and endogenous (2) S100A1 expression.

FIG. 13 AAV6/S100A1 construct used for gene therapy in HF. Shown are the positions of the two independent transgenic cassettes including the marker gene GFP driven by the CMV promoter and S100A1 driven by the.

DETAILED DESCRIPTION OF THE INVENTION

Figure 1:
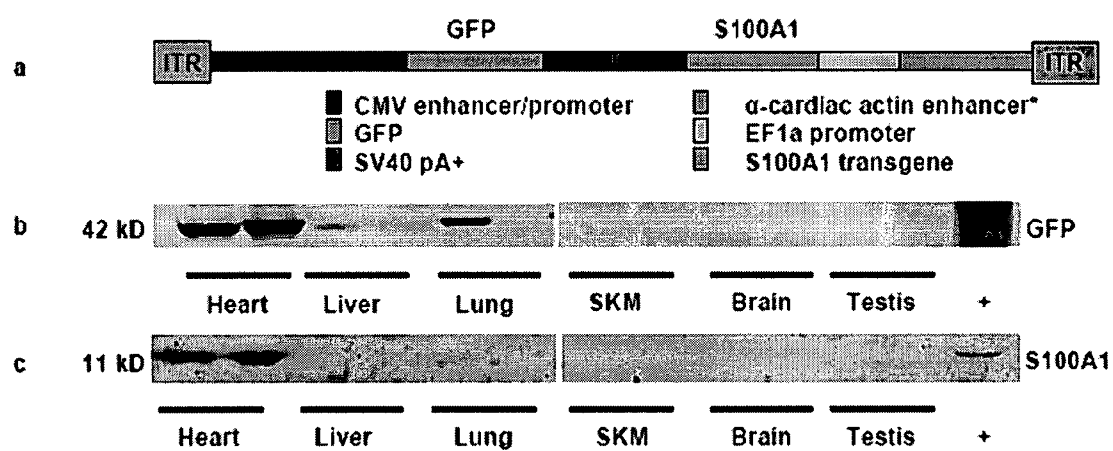
FIG. 1: Cardio-selective rAAV6-mediated in vivo gene transfer. (a) AAV6/S100A1 construct used for gene therapy in HF. Shown are the positions of the two independent transgenic cassettes including the marker gene GFP driven by the CMV promoter and S100A1 driven by the α-cardiac actin enhancer-EF1α promoter. (b) Representative Western blot analysis of GFP expression in several rat tissues 8 weeks after in vivo intracoronary delivery with AAV6/S100A1. (c) Representative Western blot of human S100A1 protein present only in the heart while absent in other rat tissues harboring the GFP transgene 8 weeks after in vivo AAV6/S100A1 delivery.

Embodiments of the present invention provide nucleic acid constructs for the specific expression of target nucleic acid in cardiac tissue or other tissue types such as endothelial cells. The constructs have additional nucleic acid sequences, other than the target nucleic acid, that support, promote and enhance the expression of target nucleic acid specifically in cardiac tissues or other tissue types. As used herein, the term "construct" and "segment are used interchangeably and they refer to a composite nucleic acid sequence comprising several different nucleic acid parts of different origin ligated together. One aspect of the present invention is directed to a nucleic acid segment that has a cardiac-specific enhancer sequence and a promoter sequence as regulatory elements joined to a multiple restriction site for insertion of a target nucleic acid. In one embodiment, the enhancer sequence contains the proximal enhancer region of the α cardiac actin gene and one or more myocyte-enhancer factor-2 (MEF2) sequences. In another embodiment, the cardiac specific enhancer sequence has a repressor sequence. In yet another embodiment, the promoter sequence is EF1α.

In a further embodiment, the cardiac tissue-specific nucleic acid segment is a gene delivery vector, including, for example, adeno-associated virus, an adenovirus, a lentivirus, a retrovirus, naked DNA, a liposome, or adeno-associated virus AAV6.

Target nucleic acids include, for example, S100A1, SERCA, FK506BP 12.6, phospholamban, inhibitory RNAs for NKX, GRK2, GRK5, or the carboxyl terminal fragment of GRK2 (βARKct).

In yet another embodiment, the enhancer sequence contains one or more enhancer MyoD consensus sequences.

In another embodiment, the enhancer comprises the sequence AGGAATTCTAAATTTACGTCTGCTTCCT-GTCAATGGGCATCCTCACTGTCAAATGCA GATGG-TACAGCAGGGCTTGGTCTCAGCCAG-GCAGGCCTCTCCCCAGTCTCCATGGCT CAGCTGTCCAGCAGTTTCATCCCTAGAC-CATCCCAAACATGGTTGAGAAGCTCTGAG GGGAG-GACCCAGCACTGCCCGGCCCCTGAAG-TATCTAATCAGCAGTCCTGCTCAGC ATATCAATCCAAGCCCACTCTAGACA-GAGATGCCGGTGCCCAGTTTTCTATTTTTAA CTGGT-GTGAACTGAAGGAAAAAGCAGCTGACTAGT (SEQ. ID. No. 1) and can include Myo D consensus sequence CAGCTG (SEQ. ID. No. 2) or an Mef2 sequence CTA(A/T)$_4$ TAG (SEQ. ID. No. 3 and 4).

In another embodiment the enhancer comprises the sequence ScnS cardiac enhancer includes the following nucleic acid: CCGGCCGGCCGTTGCTGAAAACCCTG-GATCCCTTGGGGGGCAAATGCTGCCTCCAG TTGCT-GCCTCTATGCCTCAGGTTTGATTTGCAC-CTCTTGTGTGAGGGCATGGGGATT GTGGGGGATTGTGGGGGCACTGGACAC-CACTCAGGCTGGGAATGTTCCCTGGAGAG GGGGGGTGGGACCCTGTCCCGTG-CAGGGCCAAATCCTGACGTATGCATGCTTCACC TTTTAATTGGAGAAAAGCCCTTCT-GTTTGAGTCTGGGATAAAATGAACGGCATCTCT TCCCATCCCTGCCCTGTGGAGGCCAGG-GAGCCGGTTGTGGTGGAAATGTCTTAAAG GGGGT-CAGTTGAAGTGTTTTTACTTTTGTGT-GTGGTGCACAGGGTAACCCCTTCATG AGGACACACCGTCTCTTGATCACT-GATATTTATGCATACACGTACACACTGGGGCAA GAGTGGGGGGGGTCACTTCATGGAC-CCTCCCCACACACACACACCTCAGTGGAGGC GAG-CATCAGCGTTTACCCGAGCCGCTGT-CAATCGTATGCGCCTGTGCAGTGGTTGGC AGTGGGGGTCGGGAATGGGGTGGGCTG-TACACTTTTGCAGATTGTGTCTTTCCCCGC CATCG-GCCTAGCTGGCTGACTACCCTGCCCTC-CGGCCGTGGCACCCCATCACACCCT GTGTTTGTCTCCCAG (SEQ. ID. No. 5) and may include the Myc transcription factor CCGGCCGGCCG (SEQ. ID. No. 6) or the Spl transcription factor G(A/T)GGGGGGT (SEQ. ID. No. 7 and 8).

In yet another embodiment the enhancer or promoter sequences are the enhancer or promoter sequences of the Pleiotropin (GenBank accession AL56812 and BC005916), Pleckstrin homology-like domain (AA576961), Collagen type XXIα1 (NM_030820), Cyclin G2 (AW134535), Ligatin (NM_006893)), FK506 bp 12.6, SOD2, SOD3, or phospholamban genes.

In another embodiment, the cardiac tissue-specific nucleic acid can contain additional regulatory sequences including additional enhancer or promoter sequences and additional multiple restriction sites for insertion of a target nucleic acid. The enhancer sequence can be an endothelial cell-specific enhancer sequence or a nucleotide sequence corresponding to Tie2 enhancer domain. The enhancer sequence can have a repressor sequence.

Encompassed in the present invention is a method of treating a subject for heart failure by administering a therapeutically effective amount of a nucleic acid segment described herein.

In one embodiment, the method can also be used in combination with administering a therapeutically effective amount of a β-blocker.

In a further embodiment, an endothelial cell-specific nucleic acid segment is a gene delivery vector, for example, an adenovirus.

Figure 13:
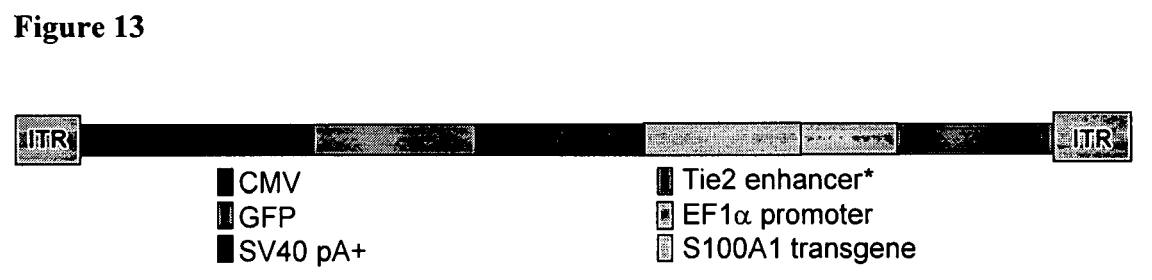

In another embodiment, the endothelial cell-specific nucleic acid segment is represented by FIG. 13. This AAV6/S100A1 construct is similar to the construct shown in FIG. 1 except the α-cardiac actin enhancer-EF1α promoter is replaced with the Tie2 enhancer.

In another embodiment, the endothelial cell-specific nucleic acid may contain additional regulatory sequences including additional enhancer or promoter sequences and additional multiple restriction sites for insertion of a target nucleic acid.

Yet another aspect of the present invention is directed to a method of treating vascular dysfunction in a subject by administering a therapeutically effective amount of the nucleic acid segment described herein. In one embodiment, the nucleic acid segment can contain, for example, the S100A1 as the target nucleic acid.

In another aspect of the present invention is directed to a method of treating hypertension in a subject by administering a therapeutically effective amount of the nucleic acid segment described herein. The nucleic acid segment can contain, for example, the S100A1 as the target nucleic acid.

Another aspect of the present invention is directed to a method of treating endothelial dysfunction in a subject by administering a therapeutically effective amount of the nucleic acid segment described herein. The nucleic acid segment can contain, for example, the S100A1 as the target nucleic acid.

Another aspect of the present invention is directed to a method of treating diabetes in a subject by administering a therapeutically effective amount of the nucleic acid segment described herein. The nucleic acid segment can contain, for example, the S100A1 as the target nucleic acid.

Yet another aspect of the present invention is directed to a method of modulating $[Ca^{2+}]_i$ in a subject by administering a therapeutically effective amount of the nucleic acid segment described herein. The nucleic acid segment can contain, for example, the S100A1 as the target nucleic acid.

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, an optional operate sequence to control transcription, a sequence encoding suitable mRNA ribosomal binding sites, and sequences to control the termination of transcription and/or translation.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation and so forth.

As used herein, a "promoter" or "promoter region" or "promoter element" used interchangeably herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "constitutively active promoter" refers to a promoter of a gene which is expressed at all times within a given cell. Exemplary promoters for use in mammalian cells include cytomegalovirus (CMV), and for use in prokaryotic cells include the bacteriophage T7 and T3 promoters, and the like.

The term "operatively linked" or "operatively associated" are used interchangeably herein, and refer to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined.

The term "coding sequence" means the nucleic acid sequence which is transcribed (DNA) and translated (mRNA) into a polypeptide in vitro or in vivo when operably linked to appropriate regulatory sequences.

As used herein, the term "vector", refers to a nucleic acid construct, designed for delivery to a host cell or transfer between different host cells or a liposome/micelle encapsulating nucleic acids for delivery to a host cell or transfer between different host cells. As used herein, a vector may be viral or non-viral vector. The vector can also be a plasmid. The vector may be an expression vector for the purpose of expressing the encoded protein in the transfected cell. A viral vector can be any viral vector known in the art including but not limited to those derived from adenovirus, adeno-associated virus (AAV), retrovirus, and lentivirus. Recombinant viruses provide a versatile system for gene expression studies, gene transfer and genome integration, and therapeutic applications.

Unless otherwise stated, the present invention can be performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.); Current Protocols in Protein Science (CPPS) (John E. Coligan, et. al., ed., John Wiley and Sons, Inc.); and Current Protocols in Immunology (CPI) (John E. Coligan, et. al., ed. John Wiley and Sons, Inc.), which are all incorporated by reference herein in their entireties.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Figure 14:
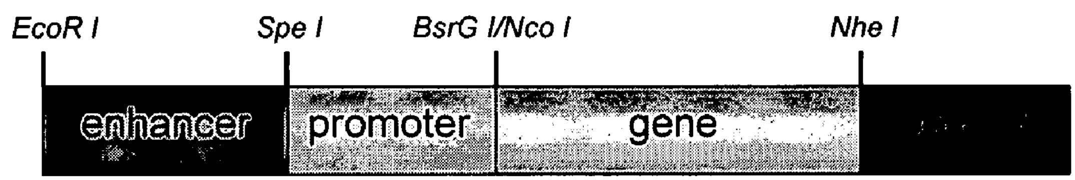
FIG. 14 A schematic diagram showing the modular design method of constructing AAV6-S100A1 gene fusion constructs. At the 5' end of the enhancer is an EcoR I restriction site and between the enhancer and the promoter there is a Spe I site, between the promoter and the 5' end of the gene there is a BsrG I and Nco I sites. Finally, at the 3' end of S100A1 after the termination codon but 3' of the polyadenylation site there is a Nhe I restriction site FIG. 15 Schematic diagrams of examples of AAV6/S100A1 constructs made using the modular design method.

The alpha cardiac actin enhancer (αCard) linked to the elongation factor 1-alpha promoter (EF1α) driving the expression of the S100A1 gene is built in a modular design. Starting in the 5' to 3' orientation, the enhancer sequence, promoter sequence, the 5100A1 coding sequence, and the polyA tail sequence are ligated in tandem via the restrictions sites: Eco RI, Spe I, BsrG I/Nco I, and Nhe I, repsectively (FIG. 14).

Figure 15:
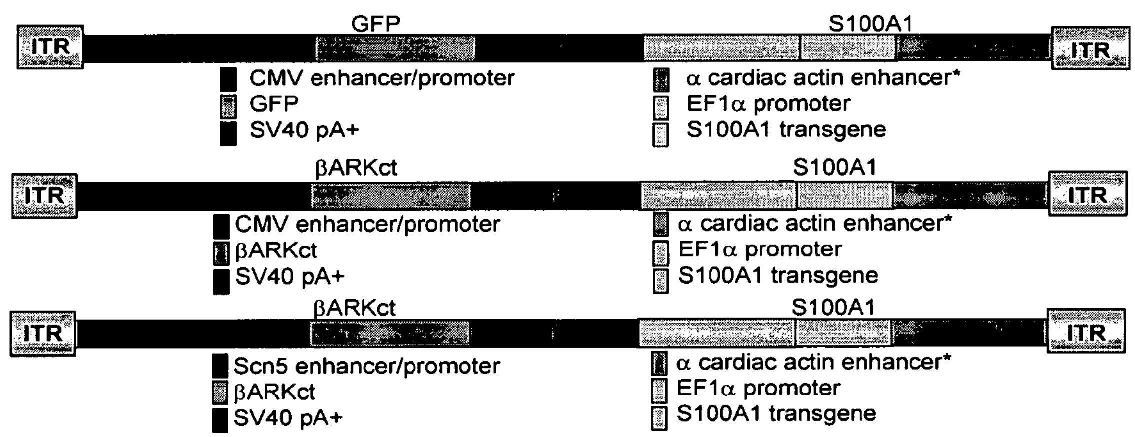

In other embodiments, alternative representations of AAV6/S100A1 constructs include but are not limited to those shown in FIG. 15.

One way to express beneficial genes after heart failure (HF) is to use the enhancer/promoters of genes whose expression is enhanced after HF to drive genes whose expression is reduced. A subsets of genes that are enhanced during HF are considered to have a fetal developmental profile. That is, these genes are normally expressed during development then expression is reduced during maturation, during HF the expression reverts to a fetal expression pattern. The genes voltage-sensitive sodium channel α-subunit (SCN5α), atrial-natriuretic factor (ANF) and cardiac ankyrin repeat protein (CARP) represents genes that show this pattern of expression. The regulatory domains of these genes contain both enhancer and repressor elements that can be substituted for the enhancer/αCard. Alternatively, portions of these enhancer/repressor domains can be cloned and ligated into the modular design disclosed herein, in addition to the present enhancer to augment its performance. For example; the use of a repressor element that decreases expression during normal cardiac function can be added to regulate the present enhancer's function.

Gene expression array data was used to identify genes whose expression is enhanced in humans after ischemic cardiomyophathy (ICM). The enhancer/promoters of these genes can augment or substitute for the enhancer/promoter in the modular design described in this application to gain more precise expression in the failing heart. These identified genes include Pleiotropin (GenBank accession AL56812 and BC005916), Pleckstrin homology-like domain (AA576961), Collagen type XXIα1 (NM_030820), Cyclin G2 (AW134535), Ligatin (NM_006893).

A number of genes whose expression is decreased after HF and their expression has been shown to have a benefit include S100A1, SERCA, FK506BP 12.6, phospholamban and the carboxyl terminal fragment of GRK2 (βARKct). These genes can be cloned in place of the S100A1 gene, or they can be cloned into the same construct to be expressed along with S100A1 as a dual expression system using separate promoter/enhancers for each gene.

The present application uses the ubiquitous EF1α promoter to drive S100A1 expression. While expression has been shown to be limited to heart tissue in rats, additional promoters can be substituted for the EF1α cassette. Several promoters are in development including the FK506 bp 12.6 and phospholamban promoters. These promoters are both small in nucleotide length and seem to be more restricted to cardiac expression than the EF1α promoter.

The 318 by αCard enhancer region already present in the construct can be augmented by the addition of nucleotides that result in decreased expression with time (e.g. CpG's for methylation) or maintenance of expression by the addition of S/MAR (lead to exposure to the nuclear matrix) can be added to upstream or downstream of the enhancer domain, again leading to augmented gene expression.

Complete exchange of the enhancer within the context of the EF1α promoter leads to gene expression within another specific region. For example, the addition of a Tie2 enhancer domain will lead to expression within the endothelium.

These nucleic acid segments are not restricted to the AAV family of viral delivery systems. Additional system, including but not limited to adenoviral, lentiviral, retroviral, naked DNA, and liposomal can be employed as alternative delivery systems depending on the application.

In one embodiment, recombinant adenovirus can be used to transfect cardiac or EC cells and produce long-term expression of S100A1 protein and other cardiovascular disease-related proteins in target cells. A simplified system for generating recombinant adenoviruses is presented by He T C. et. al. Proc. Natl. Acad. Sci. USA 95:2509-2514, 1998. The appropriate nucleic acid segments can be made in a shuttle vector, e.g. pAdTrack-CMV. The resultant plasmid is linearized by digesting with restriction endonuclease Pme I, and subsequently cotransformed into *E. coli*. BJ5183 cells with an adenoviral backbone plasmid, e.g. pAdEasy-1 of Stratagene's AdEasy™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenovirus are generated within the HEK 293 cells.

In another embodiment, a recombinant lentivirus can be used for the delivery and expression of the S100A1 and other cardiovascular disease-related proteins disclosed herein in mammalian cells. The HIV-1 based lentivirus can effectively transduce a broader host range than the Moloney Leukemia Virus (MoMLV)-base retroviral systems. Preparation of the recombinant lentivirus can be achieved using e.g. the pLenti4/V5-DESTT™, pLenti6N5-DESTT™ or pLenti vectors together with ViraPower™ Lentiviral Expression systems from Invitrogen.

In yet another embodiment, a recombinant adeno-associated virus (rAAV) can be used for the expression of the S100A1 and other cardiovascular disease-related proteins disclosed herein. Because AAV is non-pathogenic and does not illicit an immune response, a multitude of pre-clinical studies have reported excellent safety profiles. rAAVs are capable of transducing a broad range of cell types and transduction is not dependent on active host cell division. High titers, $>10^8$ viral particle/ml, are easily obtained in the supernatant and $10^{11}$-$10^{12}$ viral particle/ml with further concentration. The transgene is integrated into the host genome so expression is long term and stable.

The use of alternative AAV serotypes other than AAV-2 (Davidson et al (2000), PNAS 97(7)3428-32; Passini et al (2003), J. Virol 77(12):7034-40) has demonstrated different cell tropisms and increased transduction capabilities. With respect to brain cancers, the development of novel injection techniques into the brain, specifically convection enhanced delivery (CED; Bobo et al (1994), PNAS 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid co-transfection of a packaging cell line: AAV vector carrying the chimeric DNA coding sequence, AAV RC vector containing AAV rep and cap genes, and adenovirus helper plasmid pDF6, into 50×150 mm plates of sub confluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Delivery vectors can also included but are not limited to replication-defective adenoviral vectors, cationic liposomes and protein-cationic peptides. For example, one study reports a system to deliver DNA in vitro by covalently attaching the surfactant associated protein B (SP-B) to a 10 kDa polylysine. See, Baatz, J., et al., PNAS USA, 91:2547-2551 (1994). See, e.g., Longmuir, et al., 1992 ASBMB/Biophysical Society abstract; Longmuir, et al., 1993 Biophysical Society abstract.

A delivery vector comprising a non-cationic lipid for cytoplasmic and/or nuclear delivery of substances wherein the vector is stable and can be used in biological extracellular fluids typically found in animals, particularly blood serum.

Liposomes, spherical, self-enclosed vesicles composed of amphipathic lipids, have been widely studied and are employed as vectors for in vivo administration of therapeutic agents. In particular, the so-called long circulating liposomes formulations which avoid uptake by the organs of the mononuclear phagocyte system, primarily the liver and spleen, have found commercial applicability. Such long-circulating liposomes include a surface coat of flexible water soluble polymer chains, which act to prevent interaction between the liposome and the plasma components which play a role in liposome uptake. Alternatively, hyaluronan has been used as a surface coating to maintain long circulation.

In one embodiment, the liposome encapsulate the nucleic acid segments or even the viral particle. In one embodiment, the nucleic acid segments are condensed with a cationic polymer, e.g., PEI, polyamine spermidine, and spermine, or a cationic peptide, e.g., protamine and poly-lysine, and encapsulated in the lipid particle. The liposomes can comprise multiple layers assembled in a step-wise fashion.

Lipid materials well known and routinely utilized in the art to produce liposomes. Lipids may include relatively rigid varieties, such as sphingomyelin, or fluid types, such as phospholipids having unsaturated acyl chains. “Phospholipid” refers to any one phospholipid or combination of phospholipids capable of forming liposomes. Phosphatidylcholines (PC), including those obtained from egg, soy beans or other plant sources or those that are partially or wholly synthetic, or of variable lipid chain length and unsaturation are suitable for use in the present invention. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC) and dimyristoylphosphatidylcholine (DMPC) are suitable phosphatidylcholines for use in this invention. All of these phospholipids are commercially available. Further, phosphatidylglycerols (PG) and phosphatic acid (PA) are also suitable phospholipids for use in the present invention and include, but are not limited to, dimyristoylphosphatidylglycerol (DMPG), dilaurylphosphatidylglycerol (DLPG), dipalmitoylphosphatidylglycerol (DPPG), distearoylphosphatidylglycerol (DSPG) dimyristoylphosphatidic acid (DMPA), distearoylphosphatidic acid (DSPA), dilaurylphosphatidic acid (DLPA), and dipalmitoylphosphatidic acid (DPPA). Distearoylphosphatidylglycerol (DSPG) is the preferred negatively charged lipid when used in formulations. Other suitable phospholipids include phosphatidylethanolamines, phosphatidylinositols, sphingomyelins, and phosphatidic acids containing lauric, myristic, stearoyl, and palmitic acid chains. For the purpose of stabilizing the lipid membrane, it is preferred to add an additional lipid component, such as cholesterol. Preferred lipids for producing liposomes according to the invention include phosphatidylethanolamine (PE) and phosphatidylcholine (PC) in further combination with cholesterol (CH). According to one embodiment of the invention, a combination of lipids and cholesterol for producing the liposomes of the invention comprise a PE:PC:Chol molar ratio of 3:1:1. Further, incorporation of polyethylene glycol (PEG) containing phospholipids is also contemplated by the present invention.

In addition, in order to prevent the uptake of the liposomes into the cellular endothelial systems and enhance the uptake of the liposomes into the tissue of interest, the outer surface of the liposomes may be modified with a long-circulating agent. The modification of the liposomes with a hydrophilic polymer as the long-circulating agent is known to enable to prolong the half-life of the liposomes in the blood Liposomes encapsulating the nucleic acid segments described herein can be obtained by any method known to the skilled artisan. For example, the liposome preparation of the present invention can be produced by reverse phase evaporation (REV) method (see U.S. Pat. No. 4,235,871), infusion procedures, or detergent dilution. A review of these and other methods for producing liposomes may be found in the text Liposomes, Marc Ostro, ed., Marcel Dekker, Inc., New York, 1983, Chapter 1. See also Szoka Jr. et al., (1980, Ann. Rev. Biophys. Bioeng., 9:467).

The use of an therapeutically effective amount of the nucleic acid segments disclosed herein for the treatment of heart failure, vascular dysfunction, hypertension, endothelial dysfunction, and diabetes should be preferably include but is not limited to a composition of the nucleic acid segments in lactated Ringer’s solution and the composition is sterile. Lactated Ringer’s solution is a solution that is isotonic with blood and intended for intravenous administration. Include are antioxidants, buffers, antibiotics and solutes that render the compositions substantially isotonic with the blood of an intended recipient. In another embodiment, the composition comprise gene delivery vectors described herein. In another embodiment, the composition also include water, polyols, glycerine and vegetable oils, and nutrients for cells, for example. Compositions adapted for parenteral administration can be presented in unit-dose or multi-dose containers, in a pharmaceutically acceptable dosage form. Such dosage forms, along with methods for their preparation, are known in the pharmaceutical and cosmetic art. HARRY’S COSMETIC LOGY (Chemical Publishing, 7th ed. 1982); REMINGTON’S PHARMACEUTICAL SCIENCES (Mack Publishing Co., 18th ed. 1990).

In one embodiment, dosage forms include pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol.

In one embodiment, other ingredients can be added, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, the administration of the nucleic acid segments or gene delivery vectors disclosed herein are by any suitable route, and means, for example, parenterally, intravenous, intra-arterial, intracranial, intracerebrospinal, intratumoral, peritoneal, by injection, by catheter, by implantation with or without a matrix or gel material, or by gradual delivery device. In one embodiment, the nucleic acid segments or gene delivery vectors described herein can be administered directly by injection.

The term "therapeutically effective amount" refers to an amount that is sufficient to effect a therapeutically significant reduction in heart failure, vascular dysfunction, endothelial dysfunction, diabetes, and hypertension symptoms as well as slow the progression of these ailments over time. The term also refers to that amount necessary to attain, at least partly, the desired effect, of reducing, ameliorating, stopping, abating, alleviating, and inhibiting the symptoms associated with heart failure, vascular dysfunction, endothelial dysfunction, diabetes, and hypertension, and also control and prevent further progression of the ailments. Such amounts will depend, of course, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art; however, that a lower dose or tolerable dose may be administered for medical reasons, psychological reasons or for virtually any other reason.

Hallmark of heart failure is loss of pumping capacity, poor blood circulation, poor blood oxygenation, poor fluid removal and hence fluid built up in the body. Symptoms of heart failure include but are not limited to shortness of breath (also called dyspnea) due to blood backing up in the lungs, persistent coughing or wheezing due to fluid accumulation in the lungs, Buildup of excess fluid in body tissues (edema), tiredness, fatigue, lack of appetite, nausea, confusion and impaired thinking due to changes in the electrolyte in the blood, and increased heart rate, the body's attempt to "make up for" the loss in pumping capacity, the heart beats faster.

In one embodiment, the nucleic acid segments described herein can be administered with other therapeutics associated with heart failure, vascular dysfunction, endothelial dysfunction, diabetes, and hypertension.

This invention is further illustrated by the following examples which should not be construed as limiting. The contents of all references cited throughout this application, as well as the figures and table are incorporated herein by reference.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean ±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Example 1

Chronic in vivo S100A1 expression in myocardial cells

Experimental Procedures

Construction of α-cardiac actin enhancer-EF1α promoter—Genomic DNA was isolated from mouse (C57/BL6) muscle and PCR amplification was performed using PfuUltra (Stratagene) with the following primer pair; forward 5'-AGGAATTCTAAATTTACGTCTGCTTCCTGTCAATGGGC-3' (SEQ. ID. No. 9) and reverse 5'-CCAGACTAGTCAGCTGCTTTTCAGTTCACACCAG-3' (SEQ. ID. No. 10). This resulted in a 324 base pair fragment containing the α-cardiac actin MEF2 domain[22]. The fragment contained an extra MEF2 element built into the forward primer and two enhancer MyoD consensus sequences. This fragment was cloned in place of the CMV enhancer sequence in pCpGLacZ (Invivogen), resulting in pCpGα-cardLacZ. The human S100A1 gene was cloned by PCR using PfuUltra (Stratagene) using the following primer pair; forward 5'-CTGCCATGGGCTCTGAGCTGGAGACGGCG-3' (SEQ. ID. No. 11) and reverse 5'-CCAGCTAGCTCATTCAACTGTTCTCCCCAGAAGAAATT-3' (SEQ. ID. No. 12). This resulted in a 290 base pair fragment that replaced the LacZ gene in pCpGα-cardLacZ, resulting in pCpGα-cardS100. This plasmid was digested with EcoRI and the 5' overhang filled in with Klenow (New England Biolabs) and cloned into pTRUFR in place of the HSVtk enhancer/promoter neo gene, resulting in a packaging construct containing CMV driving GFP and α-cardiac actin enhancer/EF1α promoter driving S100A1 (see FIG. 1*a*).

AAV construct production and purification—All viruses were produced using the triple transfection technique[35]. HEK293 cells were plated at $1\times10^7$ cells/15 cm plate one day prior to transfection. Polyethyleneimine (Linear PEI, MW 25 kDa, Aldrich) was used as the transfection reagent. For each 15-cm plate the following reagents were added 12 ug-XX6-80[36], 10 μg-pXR6[37], and 6 μg-pTRUFR[35] or pTRGFPαCardS100. These DNA's were combined in 500 μl of DMEM without serum or antibiotics and 100 μl of PEI reagent (1 mg/ml pH5.0) was added, mixed and set aside for 5 min. Without changing the media, the DNA-PEI reagent was added to the cells drop-wise. Cells were then harvested 48-72 hrs after transfection and collected by centrifugation and the cell pellets were resuspended in water and freeze-thawed once prior to sonication (Branson Sonifier 250, VWR Scientific). DNase I (Sigma, Mo.) and $MgCl_2$ were then added before incubating at 37° C. for 60 min. The viruses were then purified by two rounds of cesium chloride isopycnic gradient centrifugation as described, followed by 3 rounds of dialysis in phosphate buffered saline (PBS) containing 5% sorbitol[37]. The viruses were aliquoted and stored at −80° C. in PBS containing 5% sorbitol. The total genome number was determined by dot blot hybridization[37].

Rat MI model and cardiac gene delivery—All animal procedures and experiments were performed in accordance with the guidelines of the IACUC of Thomas Jefferson University.

MI was induced as described previously using a model of cryoinfarction that produces a highly reproducible loss of myocardium[13]. Briefly, anesthetized adult male (250-300 g) rats were intubated and mechanically ventilated and anaesthesia was maintained using a 2% isoflurane (v/v) oxygen mixture. The heart was exposed through a median sternotomy and the pericardium was opened. A 6-0 suture was placed at the apex of the LV. An 8 mm diameter cylindrical stamp was cooled in liquid nitrogen and then pressed on the LV free wall. Cryothermia was applied by use of three freeze cycles of 1 min each that was interrupted by one minute thawing intervals[13,15].

Myocardial gene transfer to 10 week post-MI rats was achieved as previously described[13,15] with some modifications. Briefly, under general anesthesia (2% isoflurane, v/v) a midline cervical incision was made and the animal was cooled to 29° C. using ice packs. A P-50 catheter (Becton Dickinson, Sparks, Md.) was advanced into the aortic root via the right carotid artery and the ascending aorta was looped using 2-0 silk. 1.2 mg adenosine was injected into the right ventricle using a 30½ G needle. Next, the ascending aorta was clamped and $2.5\times10^{11}$ particles of the AAV construct and 8 μg of substance P (Sigma) were rapidly injected into the aortic root allowing for coronary perfusion. After 2 min the aortic clamp was released, a bolus of dobutamine (30 μg; intraarterial) was administered and the animal was re-warmed using a heating pad. The incision was closed and animals were transferred back to their cages receiving appropriate analgesia.

In vivo gene therapy efficiency—Percentage of GFP-stained isolated myocytes was assessed 8 weeks following AAV6/GFP (n=6) or AAV6/S100A1 (n=6) in vivo gene delivery to HF rats using an Olympus IX 71 microscope, a mercury arc light and suitable filters. Moreover, transfection efficiency of in vivo gene transfer was assessed by GFP fluorescence (510 nm) in cryosectioned hearts (20 μm) using an Olympus IX81 confocal microscope as described previously[15].

Immunohistochemistry—Immunohistochemistry was performed as described previously[13]. LV cryosections (10 μm) from AAV6/S100A1 and AAV6/GFP treated hearts were permeabilized and incubated with rabbit anti-S100A1-AB (SA 5632, custom-made). A peroxidase-conjugated secondary antibody and Vector VIP peroxidase substrate kit (Vector Laboratories, Burlingame, Calif., USA) were used to reveal the antigen. Rabbit IgG (Santa Cruz Technologies, Santa Cruz, Calif., USA) was used as negative control.

β-AR blockade—Treatment with the $\beta_1$-AR selective antagonists metoprolol was initiated 10 weeks post-MI by administration of 2 g metoprolol per liter in drinking water (approximate dose of 250 mg/kg/day) in subgroups of HF/GFP and HF/S100A1 as described previously[27]. Metoprolol was started at one fourth of the full dose and dosages were doubled every week until administration of full dose was achieved.

Echocardiography—To measure global cardiac function, echocardiography was performed 10 and 18 weeks post-MI by use of the VisualSONICS VeVo 770 imaging system with a 710 scanhead in anesthetized animals (2% isoflurane, v/v). The internal diameter of the LV was measured in the short-axis view from M-mode recordings in end diastole and end systole. VisualSONICS analysis software was used to calculate ejection fraction (EF) and fractional shortening (FS) using the formulas as previously described[13,15]. The 10 week echocardiographic data includes those animals which completed the whole study.

Catheter-based in vivo hemodynamic measurements—Cardiac function was measured 8 weeks following gene therapy (18 weeks after MI) in anesthetized rats (2% isoflurane; v/v) using 2 F pressure catheter (SPR-320; Millar instruments, Houston, Tex.). The pressure transducer was placed into the LV cavity through the right carotid artery and the right external jugular vein was cannulated with a P-10 catheter (Becton Dickinson, Sparks, Md.) that was used for isoproterenol administration (333 ng/kg BW) as previously described[13,15].

Isolation of adult rat ventricular cardiomyocytes—$Ca^{2+}$-tolerant adult cardiomyocytes were isolated from LVs 8 weeks after gene delivery (18 weeks post-MI) by a standard enzymatic digestion procedure and cultivated as described[13,15]. Cardiomyocytes used for simultaneous contractility and $Ca^{2+}$ measurements were plated with a density of 20,000 cells/cm$^2$ on laminin-coated glass dishes. For analysis of mRNA expression, cardiomyocytes were plated on laminin-coated plastic dishes (NUNC; Ø3.5 cm) with a density of 150,000 cells/cm$^2$. Length of isolated cardiomyocytes was determined on enlarged digital photos using Olympus Fluoview 4.3 software.

$Ca^{2+}$-transient analyses and contractile parameters of isolated adult rat cardiomyocytes—Contractility and intracellular $Ca^{2+}$-transients of Fura 2-AM loaded (0.5 μmmol/L for 20 minutes at 37° C.) adult rat cardiomyocytes were measured simultaneously two hours following myocyte isolation using the IonOptix MyoCam system (IonOptix Corporation)[13]. Myocytes were electrically stimulated with a biphasic pulse to contract at 37° C. Measurements were carried out using an inverse Olympus microscope (IX 71) with a dual-excitation single-emission fluorescence photomultiplier system and a video edge detection system (IonOptix Corporation). Twenty consecutive steady-state twitches for each myocyte at 1 Hz and 2.5 mM $[Ca^{2+}]_e$ were averaged and analyzed. Myocytes were isolated from 3 rats of each group (HF/S100A1, HF/S100A1+β-blocker, HF/GFP, HF/GFP-β-blocker, HF/Saline and Sham). At least 10 myocytes per animal were measured. Within the HF/AAV6-S100A1 and HF/AAV6-GFP groups GFP staining was used in order to differentiate between infected and non-infected myocytes isolated from the same animal.

Measurement of infarct size—Infarct size was examined in all groups 18 weeks post-MI. Briefly, hearts were frozen in liquid nitrogen and sectioned from apex to base into 2 mm slices. To delineate the infarct size, sections were incubated in 1% (wt/vol) TTC (Sigma) in PBS (pH 7.4) at RT for 15 min. For each section, the infarct size of the LV was calculated from enlarged digital photos using SigmaScan 5.0 software as described previously[12,15].

Western blot analysis—Western blots were performed as described previously[13,15]. Samples of liver, lung, gastrocnemius muscle, brain, testis and whole LV were homogenized at 4° C. in 3 w/v PBS with 5 mM EDTA, 5 mM EGTA and protease inhibitor mixture (1836170, complete Mini EDTA free, Roche Diagnostics GmbH, Germany) and centrifuged at 15,000 g for 15 min. Supernatant protein was subjected to electrophoresis, transferred to a PVDF membrane, and probed with either anti-S100A1-Ab (SA 5632, custom-made; detecting the human isoform of S100A1 but not the endogenously expressed rat S100A1 under the applied conditions), anti-S100A1-AB (Acris; SP5355P, detecting both human and rat S100A1) or anti-GFP-AB (Rockland). In addition to Bradford analysis probing against rabbit anti-Actin-AB (Sigma, A-2066) was used in all western blots to control equal loading.

RNA isolation and real-time RT-PCR—Total RNA was isolated from LV as well as from isolated cardiomyocytes using either Ultraspec® (Biotec) or Trizol® (Life Technologies). cDNA was synthesized by reverse transcription of the RNA with Superscript II® (Life Technologies) as recommended. Real-time RT-PCR was performed in duplicates with a 1:100 dilution of the cDNA on a MyIQ real time PCR detection system (BioRad) with the SYBR® Green PCR master mix (Applied Biosystems) as described previously[13,15]. The oligonucleotide primers to examine expression of genes were as follows: ANF, forward primer 5'-TGCCGGTAGAAGATGAGGTC-3' (SEQ. ID. No. 13), reverse primer 5'-TGCTTTTCAAGAGGGCAGAT-3' (SEQ. ID. No. 14); SERCA2a, forward primer 5'-TGAGACGCTCAAGTTTGTGG-3' (SEQ. ID. No. 15), reverse primer 5'-ATGCAGAGGGCTGGTAGATG-3' (SEQ. ID. No. 16); PLB, forward primer 5'-TACCTCACTCGCTCGGCTAT-3' (SEQ. ID. No. 17), reverse primer 5'-GATGCAGATCAGCAGCAGAC-3'(SEQ. ID. No. 18); S100A1, forward primer 5'-CGATGGAGACCCTCATCAAC-3' (SEQ. ID. No. 19), reverse primer 5'-TGGAAGTCCACCTCCCCGTC-3' (SEQ. ID. No. 20); TGF-131, forward primer 5'-GGCACAGGTGTTGAGCCCTTTCCA-3' (SEQ. ID. No. 21), reverse primer 5'-CAGGTGTTGAGCCCTTTCCA-3'(SEQ. ID. No. 22); Collagen type I, forward primer 5'-CCAGTTCGAGTATGGAAGCGA-3' (SEQ. ID. No. 23), reverse primer 5'-AGGTGATGTTCTGGG-3'(SEQ. ID. No. 24); GRK2, forward primer 5'-CCCTCTCACCATCTCTGAGC-3' (SEQ. ID. No. 25), reverse primer 5'-CGGTTGGGGAACAAGTAGAA-3' (SEQ. ID. No. 26). For normalization, 18S rRNA was used, forward primer 5'-TCAAGAACGAAAGTCGGAGG-3' (SEQ. ID. No. 27), reverse primer 5'-GGACATCTAAGGGCATCAC-3' (SEQ. ID. No. 28). PCR conditions were 95° C., 3 min, and 40 cycles of 95° C., 10 sec; 60.5° C., 45 sec. Specificity of PCR products were confirmed by gel electrophoresis.

Statistical analysis—Data are expressed as means±SEM. Unpaired student's t test and one way repeated ANOVA measures including the Bonferroni test for all subgroups were performed for statistical comparisons when appropriate. For all tests, a value of $P<0.05$ was accepted as statistically significant.

Results

Cardioselective S100A1 gene delivery using novel α-cardiac actin enhancer—To engineer a putative myocardial-selective promoter, a 316 base pair fragment of the α-cardiac actin gene enhancer containing two MEF2 sequences and two enhancer MyoD consensus sequences was amplified from mouse genomic DNA and ligated to the EF1α promoter within an AAV shuttle plasmid (FIG. 1*a*). The human S100A1 cDNA was then cloned into this plasmid. The final construct (AAV6-S100A1) also contains a separate transgene cassette with the CMV promoter driving expression of the green fluorescent protein (GFP) marker gene (FIG. 1*a*). To first examine whether this vector supports stable cardiac expression in vivo, AAV6-S100A1 was delivered to normal rats (n=4) via intracoronary delivery[13,15]. Eight weeks after gene delivery, rats were sacrificed and the heart and several other tissues were harvested and homogenized to examine long-term and tissue selective transgenic protein levels via Western blotting. Consistent with a CMV-driven transgene, GFP expression was found outside the heart with appreciable levels in liver, lung and skeletal muscle (FIG. 1*b*). Importantly and in contrast to these findings, the human isoform of S100A1 was detectable only in cardiac homogenates indicating that S100A1 expression driven by the combination of the α-cardiac actin enhancer and the EF1α promoter is indeed cardio-selective (FIG. 1*c*).

Notably, infection of myocardium by the novel AAV6 vector as assessed by GFP fluorescence of cardiac sections was global in nature but not homogenous throughout the heart (data not shown), which is consistent with previous gene delivery characteristics supported by the intracoronary delivery method[13,15]. This distribution pattern was also evident with S100A1 expression as confirmed by immunohistochemistry using an antibody specific for the human isoform of S100A1 (data not shown).

Figure 2:
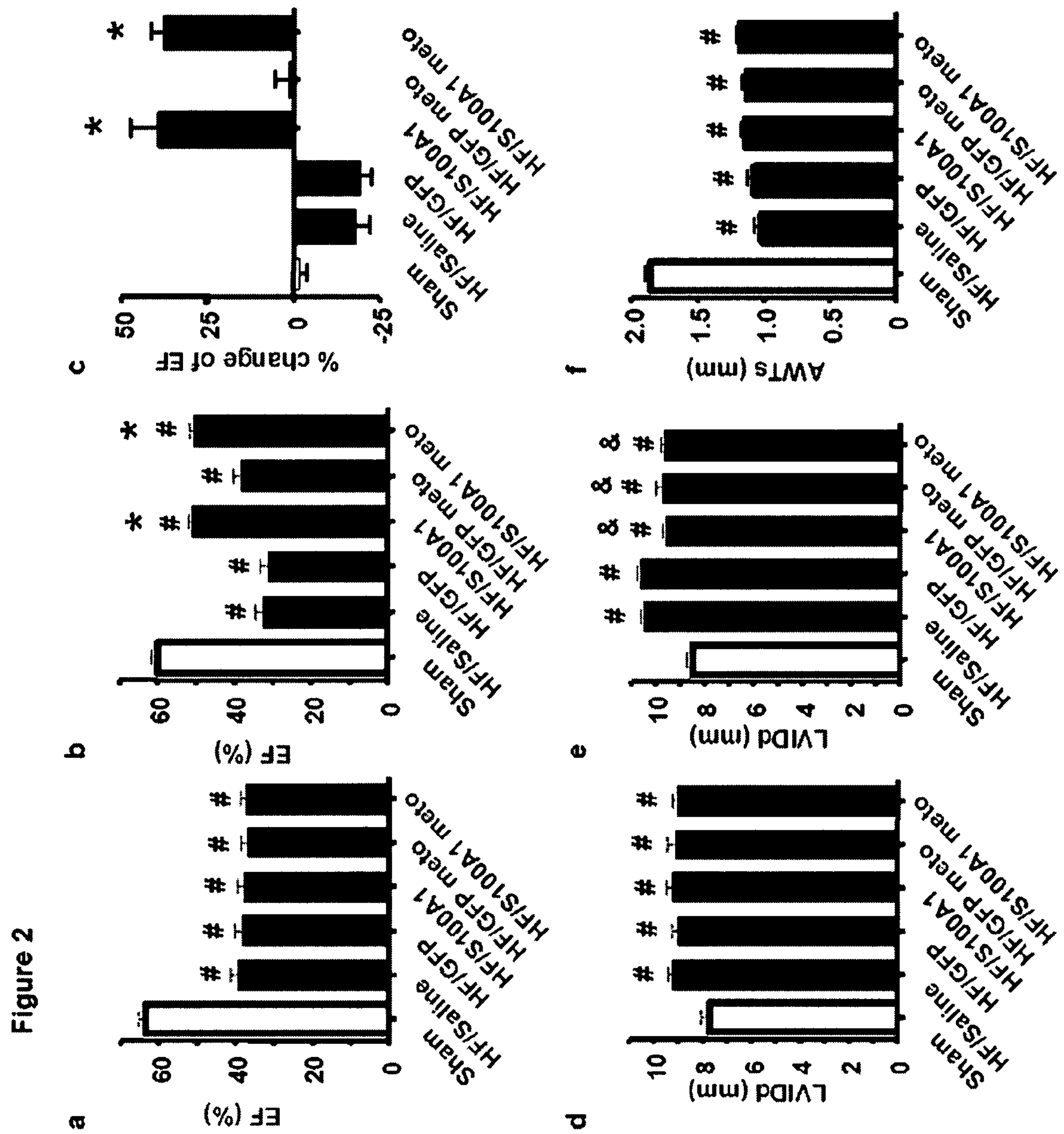
FIG. 2: S100A1 gene therapy recovers cardiac function in HF. (a) Ejection fraction (EF %) 10 weeks after MI prior to gene treatment and (b) 8 weeks following in vivo intracoronary AAV6/S100A1 gene delivery with or without metoprolol treatment. (c) % change of alteration of EF after the 8 weeks treatment period. (d) LV chamber dimensions were similar prior to gene delivery in all randomized groups. (e) Effect of AAV6/S100A1 and/or β-blocker treatment on LV chamber dimensions after 8 weeks of treatment. (f) AWTS 18 weeks after MI. Sham; n=11, HF/Saline; n=14, HF/GFP; n=11, HF/S100A1; n=12, HF/GFP-meto (beta); n=9 and HF/S100A1-meto (beta); n=9. # P<0.05 compared to Sham. * P<0.05 compared to HF/Saline, HF/GFP or HF/GFP-meto groups. & P<0.05 vs. HF/Saline or HF/GFP groups. ANOVA analysis and Bonferroni test between all groups. Data is presented as mean±SEM. Bar 8 mm. (g) Representative raw traces of M-mode echocardiography 8 weeks after gene delivery (18 weeks post-MI) in the 6 experimental groups.

Characterization of cardiac dysfunction post-MI and prior to gene delivery—A cryo-infarct model was used to induce chronic HF in rats which leads to LV dysfunction and fulminate HF in 10-12 weeks[13]. Ten weeks after MI global cardiac function was assessed to determine pre-gene therapy status in these rats compared to sham animals that did not receive a MI. All MI rats were found to have significant LV dysfunction and were randomized into 5 separate treatment groups (FIG. 2). Global cardiac failure was evident due to significantly diminished ejection fraction (EF) as compared to sham animals (FIG. 2*a*). Moreover, significant post-MI remodeling was apparent as determined by LV dilatation (FIG. 2*d*). Importantly, all post-MI rats had similar dysfunction and remodeling (FIG. 2 and data not shown) and thus, all randomized groups had the same pre-gene therapy HF status.

In addition to treating HF rats with intracoronary delivery of the novel AAV6-S100A1 vector and comparing results to HF rats treated with AAV6-GFP alone, separate groups were also treated with the $\beta_1$-adrenergic receptor (AR) antagonist, metoprolol, (meto, 250 mg/kg/day in the drinking water) beginning 10 weeks post-MI. Overall, there are 6 experimental groups: (1) sham animals with no MI (Sham, n=13); (2) HF rats treated with intracoronary injection of saline (HF/Saline, n=15); (3) HF/GFP (n=15); (4) HF/S100A1 (n=14); (5) HF/GFP and metoprolol (meto, n=13); (6) HF/S100A1 and meto (n=13) (FIG. 2). All groups were then followed over the next 2 months to assess the chronic effects of S100A1 gene transfer with and without βAR blockade.

S100A1 gene therapy chronically improves in vivo cardiac function and reverses LV remodeling in HF—The in vivo functional consequences of chronic cardio-selective S100A1 gene therapy in HF were determined by echocardiography as well as with close-chest cardiac catheterization after 2 months. All 5 HF groups still had significantly impaired cardiac function compared to sham rats (FIGS. 2*b*, 2*e*, and 2*f*) at 18 weeks after MI, however, rats treated at 10 weeks post-MI with S100A1 had significantly improved cardiac function as assessed by % EF (FIGS. 2*b* and 2*c*). Of interest, the significant ~30% improvement in global cardiac function after 8 weeks of cardiac-selective S100A1 expression was seen with or without metoprolol (FIG. 2*c*). In contrast to this improvement with S100A1, HF rats treated with only GFP or saline had further deterioration of cardiac function over the course of the 2 month treatment period (FIG. 2*c*). In HF rats treated with metoprolol only (with GFP) there was no improvement but also there was no further decline in cardiac function (FIG. 2*c*). Thus, βAR blockade appears to, at least under these conditions, halt disease progression.

Specifically concerning LV dimensions and cardiac remodeling, both cardiac S100A1 gene therapy as well as β-blocker treatment significantly attenuated further LV chamber dilatation as measured by 18 week post-MI LV diastolic dimension compared to pre-treatment (10 week post-MI) values, while there was progressive dilatation in saline and GFP treated HF rats (FIGS. 2*d* and 2*e*). Similar data was seen in the thickness of the posterior LV wall (data not shown). S100A1 expression with concurrent metoprolol treatment did not further attenuate LV remodeling over either treatment alone (FIG. 2*e*). Finally, as expected the thickness of the anterior wall (AWT, site of the infarct) was similarly thinned in all HF groups at 18 weeks post-MI and unchanged after treatment (FIG. 20, which is not surprising since gene delivery was performed 10 weeks after MI when expansion and scaring of the infarct are complete[20,21].

Figure 3:
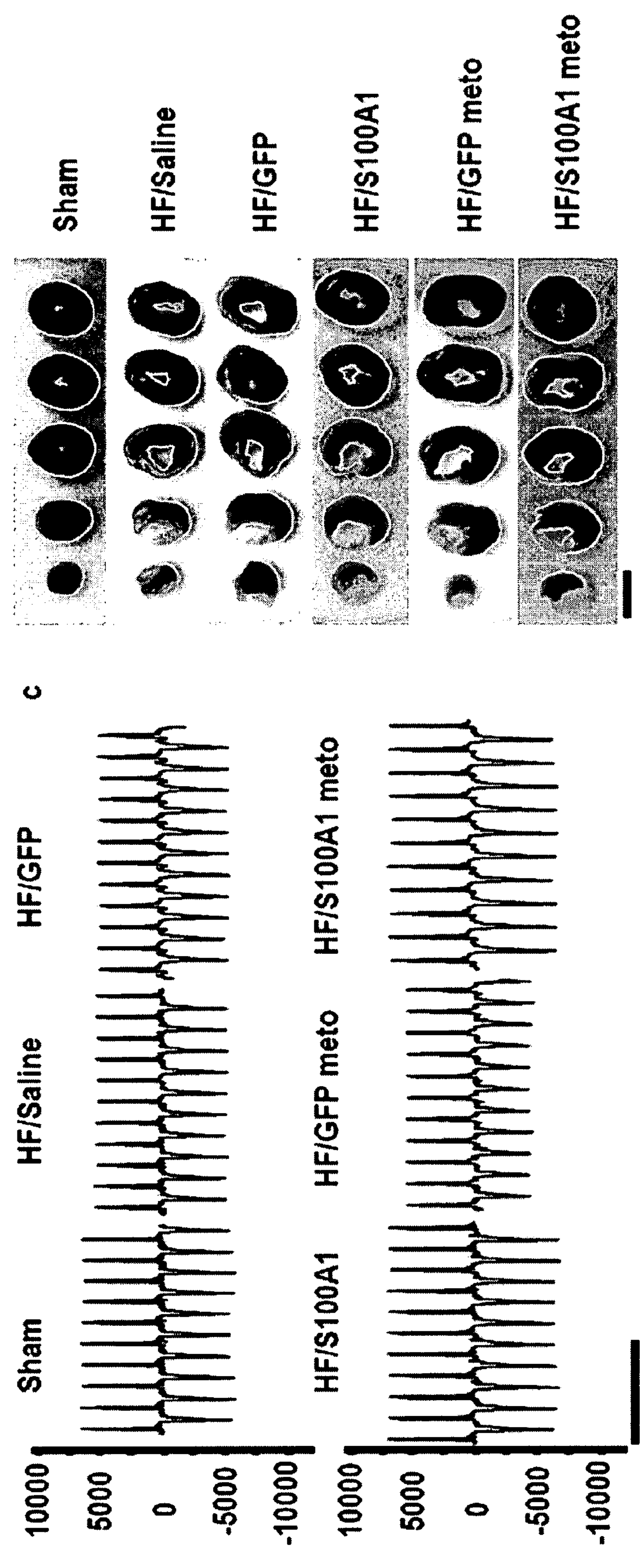
FIG. 3: AAV6/S100A1 gene therapy rescues cardiac function in HF. (a) Representative raw traces of dP/dt values 8 weeks following intracoronary delivery of AAV6/S100A1 in the 6 experimental groups (18 weeks post-MI). Bar 1 sec. (b) Western blot from representative (3 per group) of Sham, HF and HF/S100A1 treated showing S100A1 protein expression levels significantly reduced in HF 18 weeks post-MI but delivery of the AAV6/S100A1 construct resulted in S100A1 over-expression in LV homogenates. (c) Representative TTC-stained cardiac cross sections 18 weeks post-MI. Scale bar 10 mm. (d) Average LV infarct size in the 5 HF groups showing similar insults (n=4; each group).

After echocardiographic assessment of cardiac function, terminal cardiac catheterization was performed to measure 18 week post-MI hemodynamics and any therapeutic benefit from the 2 months of S100A1 gene or β-AR blocker treatment. As expected, LV contractility and relaxation as measured by the maximal rate of LV pressure rise (+dP/dt) and fall (−dP/dt), respectively was significantly reduced in failing hearts treated with either saline or GFP compared to the Sham group (Table 1). Moreover LV systolic pressure (LVSP) was significantly reduced in HF/Saline and HF/GFP groups, while end-diastolic pressure (EDP) was significantly increased in these HF rats compared to sham animals (Table 1). Representative in vivo LV dP/dt tracings from each experimental group is shown in FIG. 3*a*. After 8 weeks of increased cardiac S100A1 expression due to AAV6-S100A1 delivery there is significant improvement in LV contractile function (FIG. 3*a*, Table 1). Interestingly, β-blocker treatment (HF/GFP-Meto) significantly reduced LVEDP although LV+dP/dt and LV−dP/dt values were similar compared to HF/Saline and HF/GFP groups (Table 1).

Cardio-selective S100A1 gene therapy in HF with or without metoprolol increased all measures of cardiac contractile function including LVSP and LVEDP over the 8 week observation period compared to other HF groups and S100A1 alone had the largest improvement in contractility (Table 1). Moreover, S100A1 gene therapy led to a restoration of global myocardial function of failing hearts in vivo since +dP/dt, −dP/dt and SEP could not be statistically distinguished from healthy, sham operated animals although the EDP remained elevated with S100A1 therapy compared to Sham (Table 1).

When failing hearts were challenged with a maximal dosage of the β-AR agonist isoproterenol, chronic S100A1 overexpression continued to improve cardiac performance in vivo as +dP/dt was increased compared to HF/Saline, HF/GFP and HF/GFP-β-blocker groups (Table 1). Interestingly, under maximal 13-AR stimulation, both β-blocker treatment as well as S100A1 gene therapy significantly decreased EDP compared to HF/Saline and HF/GFP groups and EDP was actually similar to Sham values (Table 1). Importantly, heart rate was not affected by MI or in gene therapy groups and therefore not responsible for the functional improvements seen with S100A1 but as expected, was significantly reduced by β-blocker treatment (Table 1).

Cardio-selective S100A1 expression was confirmed by Western blotting and levels from whole heart homogenates can be seen in FIG. 3*b* where in HF (18 weeks post-MI) there is significant loss of cardiac S100A1 protein levels compared to sham levels and AAV6-S100A1 gene delivery driving S100A1 expression only in the heart with the α-cardiac actin enhancer/EF1α promoter not only restored normal S100A1 levels but an increase in S100A1 protein expression was observed (FIG. 3*b*). S100A1 protein overexpression was not evident in other tissues in HF rats while GFP had the same expression pattern in rat tissues outside the heart as in FIG. 1 (data not shown).

To determine if all hearts had similar injury 18 weeks post-MI, LV infarct size was assessed within a sub-set of hearts from each group (n=4) via triphenyltetrazolium chloride (TTC) staining. Representative TTC-stained cardiac sections from each group are shown in FIG. 3*c* and importantly, the left anterior free wall was thinned and LV chamber dilation was present in all HF groups. Analysis revealed an average infarct size of 22.9±0.9% of the LV (33.2±1.4% of the LV free wall), which was similar in all groups (FIG. 3*d*).

Figure 4:
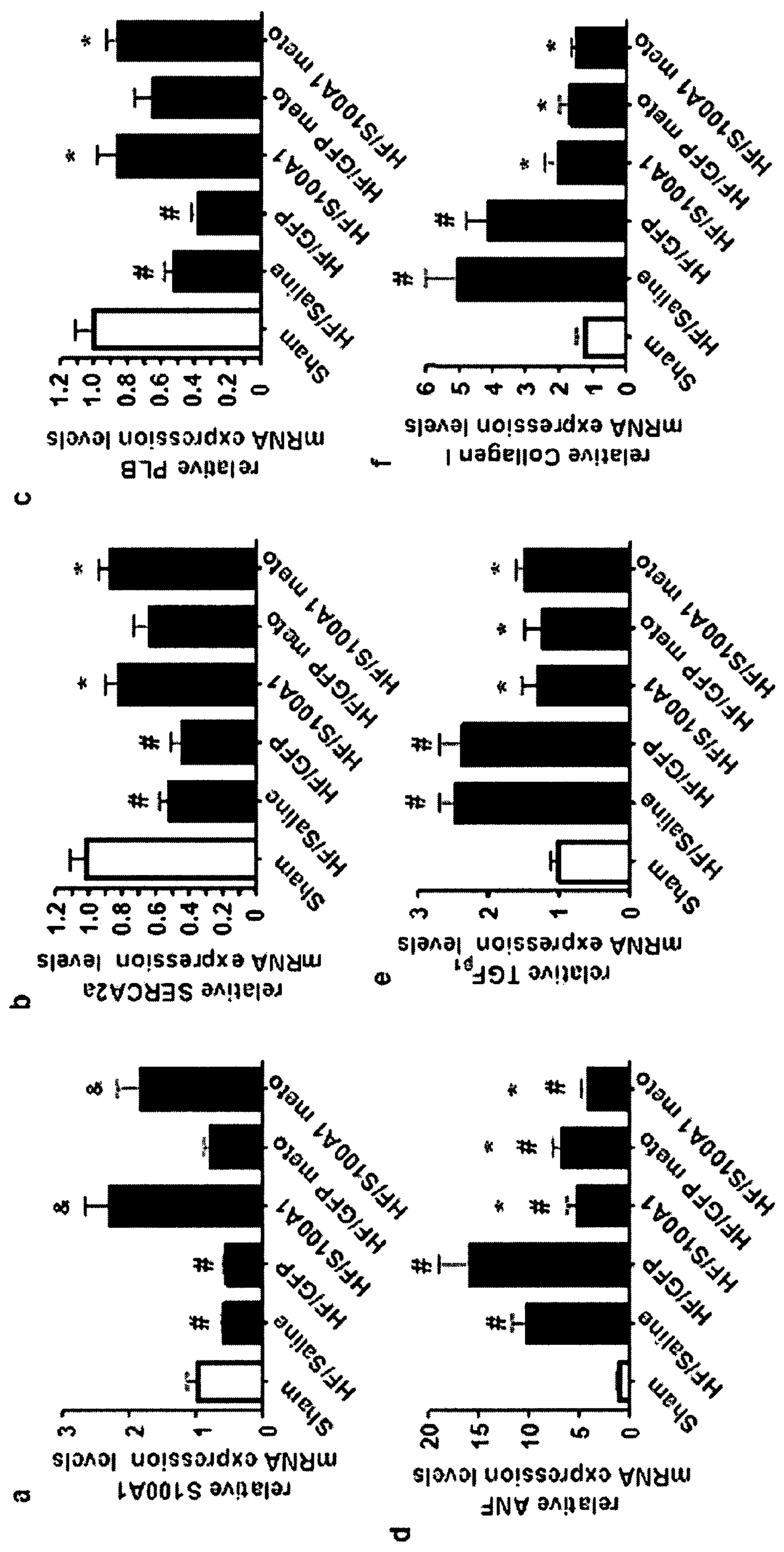
FIG. 4: Effect of S100A1 gene therapy and/or β-blocker treatment on cardiac expression of key genes. (a) Relative LV S100A1 mRNA expression in the 6 groups measured via RT-PCR. Also measured were, (b) SERCA2a mRNA, (c) PLB mRNA, (d) ventricular ANF mRNA, (e) TGFβ1 and (f) Collagen I mRNA. Expression levels in all groups, Sham (n=6), HF/Saline (n=8), HF/GFP (n=8), HF/S100A1 (n=7), HF/GFP-meto (n=6) and HF/S100A1-meto (n=6), were standardized to amplified 18S rRNA and HF levels compared to sham values as the control. # P<0.05 compared to Sham. * P<0.05 compared to HF/Saline or HF/GFP groups. & P<0.05 compared to Sham, HF/Saline, HF/GFP or HF/GFP-meto groups. ANOVA analysis and Bonferroni test between all groups. Data is presented as mean±SEM.

Analysis of representative $Ca^{2+}$-cycling proteins in HF and treated rats—Hearts removed at the end of the 18 week study made it possible to examine gene expression of key $Ca^{2+}$ cycling molecules associated with cardiac function/dysfunction within the 6 experimental groups. Chronic S100A1 gene therapy in HF significantly increased cardiac S100A1 mRNA as expected and expression was indeed significantly decreased in HF groups (FIG. 4*a*). In addition, SERCA2a and PLB mRNA levels were significantly decreased in HF/Saline and HF/GFP groups 18 weeks post-MI compared to sham and interestingly, both β-blocker and AAV6/S100A1 treatment attenuated the down-regulation of these key SR-$Ca^{2+}$ cycling molecules in HF (FIG. 4*b-c*). In fact, AAV6/S100A1 gene therapy resulted in significantly elevated SERCA2a and PLB levels that were statistically undistinguishable compared to Sham levels (FIG. 4*b-c*), while metoprolol administration attenuated the down-regulation of SERCA2a, PLB as well as S100A1 in HF to a lesser degree (FIG. 4*a-c*).

Cardioselective AAV6/S100A1 treatment in HF also reduces cardiac hypertrophy—parameters of post-MI cardiac hypertrophy was also investigated in the 6 experimental groups and found important differences. First, the heart weight to body weight ratio (HW/BW) was found to be significantly increased in all HF groups compared to Sham but the post-MI increase in HW/BW was significantly attenuated with metoprolol treatment as well as S100A1 gene therapy (Table 1). Consistent with these gross changes, ventricular ANF mRNA expression typically associated with cardiac hypertrophy was significantly increased 18 weeks post-MI in all analyzed groups compared to Sham (FIG. 4*d*). However, both β-blocker treatment and S100A1 gene therapy significantly reduced cardiac ANF expression in HF (FIG. 4*d*). On the cellular level cardiac hypertrophy was reflected by a significant increased length of isolated cardiomyocytes 18 weeks post-MI, which interestingly was significantly reduced only in AAV6/S100A1 groups (Table 1). Finally, the cardiac mRNA levels of $TGF_{\beta1}$ and Collagen I mRNA were examined as molecular markers of remodeling and both were significantly elevated in HF/Saline and HF/GFP groups (FIG. 4*e-f*). Importantly, $TGF_{\beta1}$ and Collagen I mRNA levels were found to be significantly reduced with metoprolol as well as chronic S100A1 gene therapy in HF (FIG. 4*e-f*).

Figure 5:
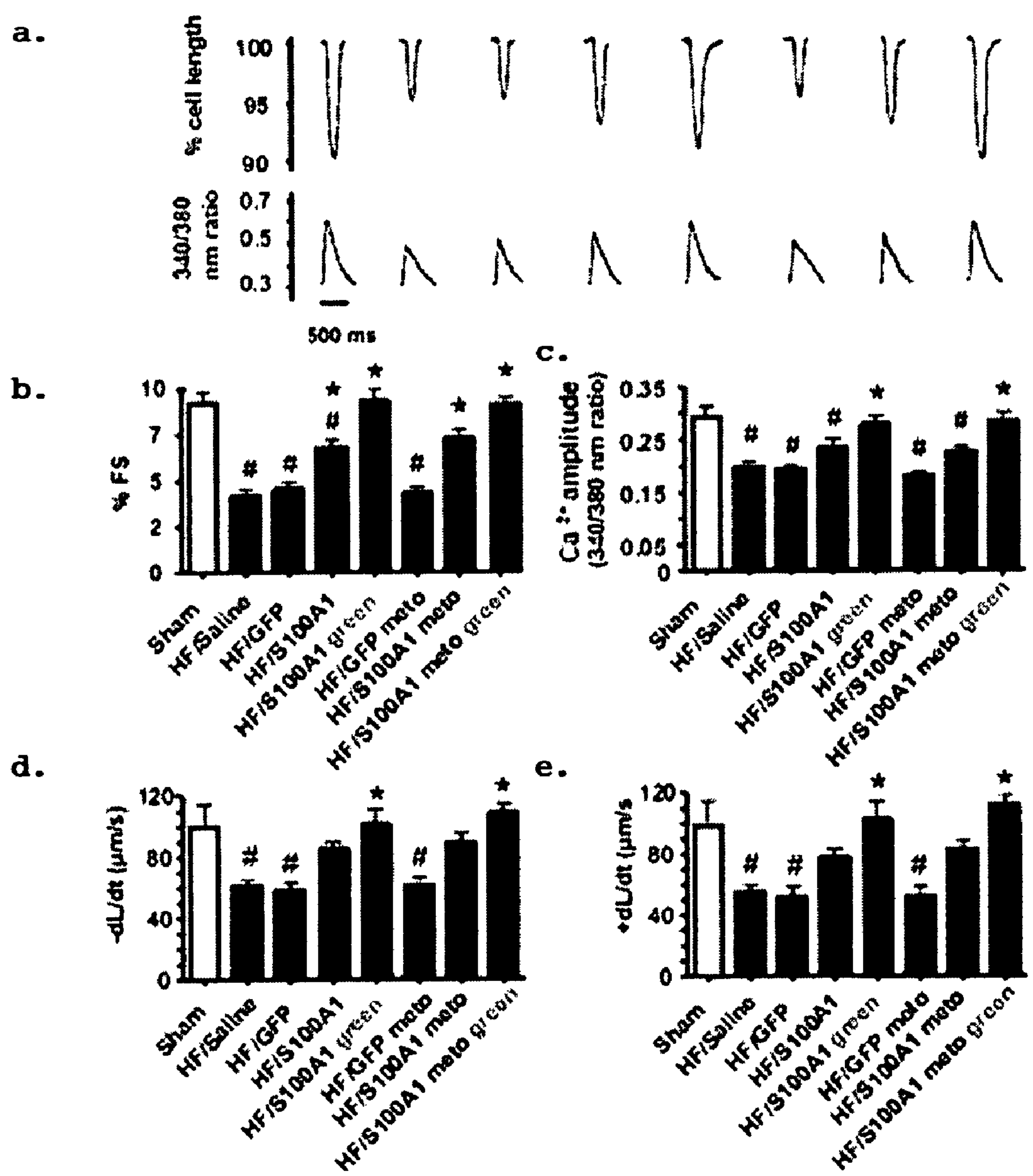
FIG. 5: Cardio-selective AAV6/S100A1 gene therapy in HF increases contractility and intracellular Ca2+-transients of isolated cardiomyocytes. (a) Representative raw traces of fractional shortening (% change in cell length, shown as downward deflection, upper panel) and original traces of representative $[Ca2+]_i$-transients (shown as upward deflection, lower panel) of (from left to right) Sham (n=39), HF/Saline (n=50), HF/GFP (n=41), HF/S100A1-non-green (n=29), HF/S100A1-green (n=22), HF/GFP-meto (n=49), HF/S100A1-meto non-green (n=27) and HF/S100A1-meto green (n=24). (b) Percentage of cell shortening (% FS). (c) Ca2+-amplitude (340/380 nm ratio), (d) rate of cell shortening (−dL/dt) and (e) rate of cell re-lengthening (+dL/dt) found in cells isolated from hearts within each experimental group. Cells were isolated from 3 different rats per group. Measurements in AAV6/S100A1 and AAV6/S100A1+Meto were taken from both green (infected) and non-green (non-infected) myocytes. # P<0.05 vs. Sham. * P<0.05 vs. HF/Saline, HF/GFP or HF/GFP-β-blocker. ANOVA analysis and Bonferroni test between all groups. Data is presented as mean±SEM.

Chronic S100A1 gene therapy increases contractile properties and $Ca^{2+}$-transients of cardiomyocytes post-MI—The contractile performance and intracellular $Ca^{2+}$-handling in freshly isolated LV cardiomyocytes from either Sham or failing hearts 8 weeks after the various treatments was investigated to explore the mechanism of chronic S100A1 gene therapy HF rescue. Two hours after myocyte isolation, GFP expression was used to identify in vivo infected cells. These markings were used to study cells containing either GFP or S100A1 or cells not infected by in vivo AAV6 gene transfer. FIG. 5*a* shows representative steady state-twitches (upper panel) and $Ca^{2+}$-transients (lower panel) of cardiomyocytes isolated from all 6 experimental groups 18 weeks after MI and 2 months after therapeutic intervention.

Myocytes isolated from Saline and GFP treated HF rats had significant decreases in fractional cell shortening (% FS; FIG.

5*b*), the amplitude of the $[Ca^{2+}]_i$ transient (FIG. 5*c*), the rate of myocyte shortening (−dL/dt; FIG. 5*d*) and the rate of myocyte relengthening (+dL/dt; FIG. 5*e*) compared to myocytes isolated from sham non-MI hearts. Interestingly, metoprolol treatment alone (+AAV6/GFP) did not affect contractile properties of isolated failing myocytes under the conditions since $[Ca^{2+}]_i$ transients, % FS, ++dL/dt and −dL/dt were similar to HF/Saline and HF/GFP groups (FIG. 5*b-e*). Importantly, data using only infected cells (green) from AAV6/S100A1 treated HF rats showed that S100A1 overexpression completely rescues myocyte dysfunction since contractile parameters as well as $[Ca^{2+}]_i$; transients were similar in these HF cells compared to non-failing myocytes (FIG. 5*b-e*). Further, the therapeutic effect on isolated myocytes from AAV6/S100A1 gene therapy in HF was preserved under additional β-blocker administration (FIG. 5*b-e*). Interestingly, non-infected cardiomyocytes (non-green) which were obtained from AAV6/S100A1 treated rats showed a trend towards improved contractile properties and $[Ca^{2+}]_i$ transients compared to HF/Saline, HF/GFP and HF/GFP-β-blocker groups (FIG. 5*b-e*). This is of potential significance since all parameters examined were similar between infected (green) and non-infected myocytes isolated from AAV6/GFP treated HF rats (data not shown) and perhaps S100A1 overexpressing cells can result in a "bystander effect" reversing dysfunction in other cardiac myocytes as well. Alternatively, GFP expression may be below detection.

The data presented in the current study demonstrates the potential clinical usefulness of a rAAV6 vector containing a cardiac-selective promoter to support chronic therapeutic gene expression in the failing heart. This novel vector in a chronic post-MI rat HF model, unambiguously demonstrates that cardio-selective S100A1 gene therapy can chronically reverse global in vivo cardiac dysfunction and attenuate LV remodeling. Notably, improved function in HF after cardio-selective S100A1 treatment remained out to at least 8 weeks following in vivo gene delivery providing evidence for a sustained therapeutic effect. Moreover, S100A1 mediated recovery of functional properties of failing myocardium were preserved with additional pharmacological βAR blocker treatment. Thus, S100A1 gene addition could represent a viable clinical approach for HF treatment and add to existing drug treatment.

The choice for directing cardiac-selective gene expression was a sequence from the proximal enhancer region of the α-cardiac actin gene. Previously, this region that contains a MEF2 sequence was shown to direct heart but not skeletal muscle expression[22]. A second MEF2 site was added in order to potentially drive stronger gene expression in the heart. As the results show, the enhancer element cloned in front of the EF1α promoter produces robust expression of S100A1 that was specifically localized to the normal and failing rat heart after in vivo intracoronary delivery. Tissue selectivity was confirmed by including a second transgene cassette in this rAAV6 vector containing CMV-GFP, and indeed GFP expression was found in several extra-cardiac sites following intracoronary delivery. This is the first demonstration of long-term, myocardial-specific gene expression after in vivo gene delivery and represents the use of a vector that could have significant clinical relevance as a beneficial means to treat chronic human HF. This example demonstrate that enhanced expression of S100A1 induces several beneficial effects chronically on the failing heart.

In the HF model, rats were found to have significant LV dysfunction and remodelling at 10 weeks post-MI, which was similar in all randomized treatment groups. Consistent with clinical HF development[23-25], cardiac contractile function further deteriorated over the 2 month treatment period in control treatment (saline and GFP only) groups. However, enhanced S100A1 expression after cardiac-selective AAV6-mediated gene delivery led to functional recovery of the failing rat heart seen globally with increased % EF and dP/dt and lower EDP and HF rescue was also seen in individual ventricular cardiomyocytes. Moreover, enhanced contractile function of S100A1-treated failing hearts was preserved under maximal β-AR stimulation further demonstrating the therapeutic potential of S100A1. Importantly, S100A1 is reduced in the failing rat heart consistent with human HF[16], and restoration to the supranormal levels responsible for the rescue seen in this study reveals a critical role for this protein in $Ca^{2+}$-dependent cardiac regulation and function.

An interesting finding at the myocyte level was that when studying only green cells (transgene expressing), there was a complete restoration of $[Ca^{2+}]_i$ transients and contractile parameters as S100A1-treated HF myocytes has similar values to healthy cells 8 weeks after gene therapy. Moreover, data from isolated cardiomyocytes also reveals a potential indirect therapeutic effect of cardiac S100A1 gene delivery on cells which were not infected in vivo since these non-GFP myocytes displayed a trend towards increased functional properties. This is especially interesting since functional recovery of the failing heart globally was achieved despite heterogeneous gene delivery. The data using GFP expression in myocytes showed approximately 40% infection rate, thus there may be an indirect effect of S100A1-overexpressing myocytes to improve the function of neighboring myocytes. Further, the reduced wall stress and regression of maladaptive hypertrophy may allow non-infected myocytes to recover on their own. Alternatively, in vivo AAV6/S100A1 gene delivery might be underestimated by GFP co-expression since brightness of GFP fluorescence varied substantially between isolated myocytes (data not shown).

To increase the clinical relevancy of the study, a β-AR blocker component was added. Metoprolol administration in HF significantly attenuated LV remodeling, reduced cardiac hypertrophy, lowered EDP and prevented further deterioration of cardiac function in HF. However, β-AR blocker treatment did not affect functional properties of isolated failing cardiomyocytes and failed to recover functional properties of in vivo global cardiac function under the conditions. These findings are in line with observations in several rodent HF and post-MI models showing that selective $\beta_1$-blockade attenuates post-MI structural remodeling without concomitant improvement in myocardial function[27-29]. Differences in contractile function between cardiomyocytes isolated from S100A1 and β-blocker treated animals might be caused by the trend towards down-regulation of SERCA2a, PLB and S100A1 expression in HF/GFP-β-blocker rats while $Ca^{2+}$-cycling was stimulated by S100A1 over-expression in HF/S100A1 groups.

Clinical studies such as the Metoprolol Controlled-Release Randomized Intervention Trial in Heart Failure (MERIT-HF) have clearly proven that, although counterintuitive, β-blocker therapy in patients with HF can not only attenuate pathological remodeling of the heart, but may actually improve patient outcomes[30,31]. Therefore, preservation of S100A1 mediated positive inotropic effects under β-blocker treatment, as observed in this study, suggests potentially additive action of both strategies and supports the clinical application of S100A1 gene therapy in HF. This coupled with the increased safety of the AAV6 vector to target S100A1 over-expression solely to myocardium produces a potential desirable situation for clinical translation of the findings. Targeted approaches to specifically treat failing cardiomyocytes are desirable in order to increase safety for patients and limit potential adverse affects of gene therapy by prevention of gene expression in other cell types or organs.

The goal of the present study was to investigate long-term actions of S100A1 in HF. This is especially important since cytosolic $Ca^{2+}$ overload and excess cAMP generation under chronic pharmacological inotropic treatment in HF are associated with increased mortality in humans and animal models[18,19,32]. Long-term positive inotropic S100A1 gene therapy resulted in recovery of contractile function in HF which was, at least largely, mediated by rescued intracellular $Ca^{2+}$-turnover and SR $Ca^{2+}$-cycling. Importantly, S100A1 protein can decrease $Ca^{2+}$-spark activity in ventricular cardiomyocytes under diastolic conditions which might contribute to prevent detrimental diastolic $Ca^{2+}$-overload and SR $Ca^{2+}$-leakage in HF[33].

To summarize, this study reports three novel findings. The first is that long-term in vivo cardio-selective S100A1 gene therapy is feasible using the α-cardiac actin enhancer/EF1α promoter in a rAAV6 vector. Second, the data show for the first time that S100A1 gene therapy can result in the chronic recovery of failing myocardium in vivo. Finally, effects of S100A1 gene therapy in HF are preserved under β-blocker treatment in vivo. Since β-blocker treatment attenuates cardiac remodeling in HF but lacks improvement of cardiac function both treatment strategies might be additive in HF.

Table 1: Hemodynamic Parameters in HF after AAV6/S100A1 gene Therapy. 8 weeks after gene therapy in HF, in vivo LV +dP/dt, −dP/dt, EDP, SEP and HR were assessed in Sham (n=11), HF/Saline (n=12), HF/GFP (n=10), HF/S100A1 (n=11), HF/GFP-meto (n=12) and HF/S100A1-meto (n=12) rats under basal conditions as well as after maximal isoproterenol stimulation. HW/BW ratio was also assessed in all groups. Also included is the diastolic cell length measured 2 hrs after cardiomyocyte isolation from 3 animals per group. Sham (n=34), HF/Saline (n=41), HF/GFP (n=43), HF/S100A1 (n=56), HF/GFP-meto (n=44), HF/S100A1-meto (n=65). # P<0.05 vs. Sham. * P<0.05 vs. HF/Saline, HF/GFP or HF/GFP-meto groups. ** P<0.05 vs. HF/Saline or HF/GFP. & P<0.05 vs. each non-β-AR blocker treated group. ANOVA analysis and Bonferroni test between all groups. Data is presented as mean±SEM.

TABLE 1

Hemodynamic Parameters in HF after AAV6/S100A1 gene Therapy.

| | Sham | HF/Saline | HF/GFP | HF/S100A1 | HF/GFP meto | HF/S100A1 meto |
|---|---|---|---|---|---|---|
| LV catheterization Basal | | | | | | |
| HR ($min^{-1}$) | 292 ± 6 | 295 ± 9 | 288 ± 7 | 288 ± 9 | 264 ± 8$^{\&}$ | 269 ± 5$^{\&}$ |
| LV +dP/dt (mmHg/s) | 6559 ± 281 | 5205 ± 295$^{\#}$ | 5066 ± 262$^{\#}$ | 6720 ± 353* | 4948 ± 225$^{\#}$ | 6390 ± 236* |
| LV −dP/dt (mmHg/s) | 6565 ± 277 | 4740 ± 284$^{\#}$ | 4416 ± 136$^{\#}$ | 5616 ± 461* | 4418 ± 223$^{\#}$ | 5450 ± 130* |
| LVEDP (mmHg) | 2.5 ± 0.4 | 8.2 ± 0.7$^{\#}$ | 6.8 ± 0.3$^{\#}$ | 3.2 ± 0.4** | 4.6 ± 0.5** | 2.4 ± 0.4** |
| LVESP (mmHg) | 128 ± 2.0 | 113 ± 2.9$^{\#}$ | 112 ± 2.5$^{\#}$ | 124 ± 4.4* | 109 ± 3.1$^{\#}$ | 118 ± 1.3 |
| Isoproterenol (333 ng/kg BW) | | | | | | |
| HR ($min^{-1}$) | 341 ± 5 | 334 ± 4 | 342 ± 7 | 349 ± 5 | 308 ± 6$^{\&}$ | 310 ± 4$^{\&}$ |
| LV +dP/dt (mmHg/s) | 14673 ± 215 | 9388 ± 215$^{\#}$ | 9105 ± 381$^{\#}$ | 11887 ± 660$^{\#}$,* | 9403 ± 491$^{\#}$ | 10808 ± 686$^{\#}$ |
| LV −dP/dt (mmHg/s) | 8039 ± 317 | 5543 ± 274$^{\#}$ | 5490 ± 378$^{\#}$ | 7566 ± 368* | 5571 ± 333$^{\#}$ | 6278 ± 302$^{\#}$ |
| LVEDP (mmHg) | 1.4 ± 0.2 | 6.8 ± 1.1$^{\#}$ | 6.1 ± 0.8$^{\#}$ | 1.3 ± 0.3** | 2.8 ± 0.4** | 2.2 ± 0.3** |
| LVESP (mmHg) | 126 ± 1.9 | 103 ± 2.3$^{\#}$ | 105 ± 4.3$^{\#}$ | 121 ± 4.6* | 105 ± 3.7$^{\#}$ | 113 ± 3.1 |
| HW/BW ratio (g/kg) | 2.5 ± 0.05 | 3.1 ± 0.05$^{\#}$ | 3.06 ± 0.04$^{\#}$ | 2.76 ± 0.08** | 2.77 ± 0.05** | 2.81 ± 0.04** |
| Cell length (μm) | 104.1 ± 2.4 | 125.9 ± 3.5$^{\#}$ | 127.8 ± 3.1$^{\#}$ | 113.9 ± 2.4* | 118.9 ± 2.3$^{\#}$ | 110.8 ± 2.3* |

Legend:

8 weeks after gene therapy in HF, in vivo LV +dP/dt, −dP/dt, EDP, SEP and HR were assessed in Sham (n = 11), HF/Saline (n = 12), HF/GFP (n = 10), HF/S100A1 (n = 11), HF/GFP-meto (n = 12) and HF/S100A1-meto (n = 12) rats under basal conditions as well as after maximal isoproterenol stimulation. HW/BW ratio was also assessed in all groups. Also included is the diastolic cell length measured 2 hrs after cardiomyocyte isolation from 3 animals per group. Sham (n = 34), HF/Saline (n = 41), HF/GFP (n = 43), HF/S100A1 (n = 56), HF/GFP-meto (n = 44), HF/S100A1-meto (n = 65).

$^{\#}$P < 0.05 vs. Sham.

*P < 0.05 vs. HF/Saline, HF/GFP or HF/GFP-meto groups.

**P < 0.05 vs. HF/Saline or HF/GFP.

$^{\&}$P < 0.05 vs. each non-β-AR blocker treated group.

ANOVA analysis and Bonferroni test between all groups.

Data is presented as mean ± SEM.

Example 2

S100A1 Expression in Endothelial Cells

Experimental Procedures

SKO mice—Mice with a deletion of the S100A1 gene (SKO) have been backcrossed into a C57BL/6 background and characterized as described previously.[11] SKO and wild-type (WT) mice of either sex and 3 months of age were used for this study. All animal procedures and experiments were performed in accordance with the guidelines of the IACUC of Thomas Jefferson University.

Isolation of mouse aortic endothelial cells—Mouse aortic endothelial cells (MAEC) from WT and SKO were obtained by outgrowth from aortic patches on a collagen matrix (Sigma) for three days in basal EBM-2 media (Cambrex, Walkersville, Md.) supplemented with vascular endothelial growth factor (VEGF) and 5% FCS as described previously.[50] MAEC were identified morphologically and phenotyped by functional uptake of acetylated LDL and immunohistochemistry against vWF. Outgrowth resulted in a mixture of cell types and proportion of EC as measured by vWF staining was ~50%. Cells were used at passage one.

Isolation of rat cardiac endothelial cells—Rat cardiac endothelial cells (RCEC) were isolated using magnetic microbeads (Miltenyi Biotech, Auburn, Calif.) ligated with an anti-rat platelet endothelial cell adhesion molecule-1 (PE-CAM-1) antibody.[51] RCEC were phenotyped by functional uptake of acetylated LDL and PECAM-1 staining.[52] RCEC were used between passage 4 and 8.

Immunofluorescence—Cells were seeded overnight on collagen-coated glass coverslips, fixed and permeabilized as described previously.[13] Human coronary endothelial cells (HCAEC; purchased from Cambrex), RCEC and MAEC were labeled with a rabbit anti-S100A1 antibody (AB) (Acris, SP5355P; 1:200) followed by a 488 donkey anti-rabbit AB (alternatively, 568 goat ant-rabbit AB, both Molecular Probes; 1:100). Co-immunofluorescence for S100A1 and sarcoplasmic reticulum (SR) $Ca^{2+}$-ATPase (SERCA2) as well as for S100A1 and the inositol 1,4,5-triphosphate receptor ($IP_3R$) was performed in RCEC using the S100A1 AB as described above and, consecutively, a goat-anti SERCA2 (sc-8095, 1:100) or a goat-anti $IP_3R$ AB (sc-7278, Santa Cruz, Calif.) followed by probing with a 488 donkey anti-rabbit and a 555 donkey anti-goat AB's (Molecular Probes; 1:100). Negative controls were done using appropriate amounts of corresponding IgG. Slides were mounted using Vectashield medium with DAPI (Vector Laboratories, Burlingame, Calif.). Images were obtained by using an Olympus IX 71 microscope, a mercury arc light and suitable filters. Background correction was performed using the appropriate negative controls.

Immunohistochemistry—Immunohistochemistry was performed as described previously.[21] Briefly, MAEC were seeded on collagen-coated glass coverslips and allowed to grow overnight in fully supplemented EBM-2 medium. Cells were incubated with rabbit anti-vWF-AB (Dako; A-0082; 1:100). A peroxidase-conjugated secondary antibody and Vector VIP peroxidase substrat kit (Vector Laboratories, Burlingame, Calif., USA) was used to reveal the antigen. Isotype rabbit IgG (Santa Cruz Technologies, Santa Cruz, Calif., USA) was used as a negative control. Additionally, aortas from WT or SKO were cryosectioned (7 μm), mounted, permeabilized and immunostained for either vWF or S100A1 (Acris, SP5355P; 1:100) as described above.

In Vitro physiology —The relaxation/contraction response of thoracic aortas of WT or SKO mice was examined using a commercially available mounting apparatus attached to a force transducer (ADInstruments). Responses of 2.5 mm rings of mouse thoracic aorta to phenylephrine (PE; $10^{-9}$-$3\times10^{-5}$ M), acetylcholine (ACh; $10^{-9}$-$3\times10^{-5}$ M) and sodium nitroprusside (SNP; $10^{-10}$-$3\times10^{-5}$ M) were tested in the presence and absence (mechanically scraped using a thin wire) of endothelial cells at 37° C. in bubbled (95% $O_2$/5% $CO_2$) Krebs-Henseleit (KH) buffer as described previously.[22] For ACh and SNP responses, pretension was established at the $EC_{50}$ of the PE response ($3\times10^{-7}$ M). Data were normalized to the PE-induced $EC_{50}$ contraction which were similar between all aorta tested.

Telemetric blood pressure measurement—Mice were anesthetized using ketamine (100 mg/kg body weight) and xylazine (5 mg/kg body weight) and a pressure transducer was placed in the aortic arch while miniaturized telemetry devices (DSI, St. Paul, Minn., USA) were implanted on the nape of the neck of the animal. After implantation of the transmitter, mice were returned to their cages. Systolic blood pressure (SBP), diastolic blood pressure (DBP), mean arterial blood pressure (MAP) and heart rate (HR) were recorded from the aortic arch in conscious, unrestrained animals daily at the same time for four days.

NO release from mouse aorta—NO release from the endothelial surface of aorta was measured in vitro using an Apollo 4000 "Free Radical Analyzer" (WPI, Sarasota, Fla.) as previously described with some modifications.[52] Briefly, thoracic aorta of WT (n=4) and SKO (n=4) mice were carefully isolated and pinned down in KH solution after connective tissue was thoroughly removed. NO was measured under baseline conditions as well as after ACh stimulation ($10^{-5}$ M). Two measurements were recorded per animal and condition and NO values were normalized to the weight of the vascular tissue.

S100A1 overexpression and NO production in HCAEC—S100A1 overexpression in HCAEC was achieved by electrical transfection of the plasmid pAdTrack-S100A1 (10 μg), which encodes for GFP and S100A1 both driven by individual cytomegalovirus (CMV) promoters. PBS and the plasmid pAdTrack (10 μg) were used as controls. 500,000 HCAEC were used for each transfection using Nucleofactor® (AMAXA biosystems) according to the manufacturers instructions and plated on 6 well dishes. 18 hours after transfection cells were stimulated using $10^{-5}$M ACh or PBS for 1 hour. A third group of transfected HCAEC were pre-incubated with the $IP_3R$ blocker 2-aminoethoxydiphenylborate (2-APB) (Cayman Chemical, Ann Arbor, Mich.) ($10^{-4}$ M) 20 minutes prior to ACh stimulation. NO in the supernatant was measured indirectly using the Nitrate/Nitrite fluorometric assay kit (Cayman, Chemical) according to company recommendations. Transfection was controlled by GFP expression as described previously and cells were harvested for mRNA isolation. Experiments were run in triplicate and 3 individual experiments were performed.

Adenoviral vectors—First-generation S100A1 adenovirus (AdS100A1) was obtained by using the pAdTrack-CMV/pAdEasy-1 system as previously described.[13,15,54] Expression of human S100A1 cDNA and green fluorescent protein (GFP) reporter gene were each driven by a CMV promoter. The same adenovirus devoid of S100A1 cDNA served as control (AdGFP). The titre of stocks determined by plaque assays were $5\times10^{11}$ pft/ml for both AdGFP and AdS100A1 respectively.

$Ca^{2+}$-transient analyses of isolated MAEC—MAEC used for $Ca^{2+}$-transient measurements were plated with a density of 20,000 cells/$cm^2$ on collagen-coated glass dishes (BT-CS Cult/stim chamber; Cellmc, Norfolk, Va.). Intracellular $Ca^{2+}$-transients of Fura 2-AM loaded (0.5 μmol/L for 20 minutes at 37° C.) MAEC were measured 4 days following cell isolation using the IonOptix MyoCam system (IonOptix Corporation) as recently described.[21] After 20 seconds of stable recording MAEC were stimulated using acetylcholine (ACh, $10^{-5}$ M) at room temperature. Measurements were carried out for 300 seconds using an inverse Olympus microscope (IX 71) with a dual-excitation single-emission fluorescence photomultiplier system and custom-made settings for endothelial cells (IonOptix Corporation). AdS100A1 (10 pfu/cell) was used to express the S100A1 protein in SKO-derived MAEC and AdGFP (10 pfu/cell) was used as a control. GFP fluorescence was used in order to confirm AdS100A1 or ADGFP infection. Notably, MAEC were identified by morphology and, importantly ACh stimulation of smooth muscle cells or fibroblasts did not result in any detectable $Ca^{2+}$-transient (data not shown). MAEC were isolated from 3 mice from each group (WT, SKO, SKO-AdS100A1/SKO-AdGFP).

Western blot analysis—S100A1 protein, heat shock protein 90 (Hsp90) and eNOS expression was assessed in cardiac tissue, blood-free lung samples from WT or SKO mice or cultured RCEC and HCAEC cells as described previously using rabbit anti-S100A1-AB (1:3000) (Acris, SP5355P), mouse anti-Hsp90 (SC-13119; 1:1000) or mouse anti-eNOS (BD Transduction, 610297; 1:1000).[13,52] In addition to Bradford analysis probing against rabbit anti-actin-AB (Sigma, A-2066; 1:1000) was used in all western blots to control equal loading.

Regulation of S100A1 expression in HCAEC—After growing HCAEC or RCEC to 90% confluency full medium was replaced by basal EBM-2 medium with 0.5% serum and cells were stimulated with endothelin-1 (ET-1), angiotensin II (AngII) (both $10^{-7}$ M) or PBS for 60 h. Cells were harvested for either mRNA or protein isolation and S100A1 expression was standardized against 18S rRNA or GAPDH.

RNA Isolation and Real-time RT-PCR—Total RNA was isolated from either HCAEC or RHEC using Trizol® (Life Technologies). cDNA was synthesized by reverse transcription of the RNA with Superscript II® (Life Technologies) as recommended. Real-time PCR was performed in duplicates with a 1:100 dilution of the cDNA on a MyIQ real time PCR detection system (BioRad) with the SYBR® Green PCR master mix (Applied Biosystems). The oligonucleotide primers to examine expression of genes were as follows: S100A1, forward primer 5'-CGATGGAGACCCTCATCAAC-3' (SEQ. ID. No. 19), reverse primer 5'-TGGAAGTCCACCTCCCCGTC-3' (SEQ. ID. No. 20). For normalization, 18S rRNA was used, forward primer 5'-TCAAGAACGAAAGTCGGAGG-3' (SEQ. ID. No. 27), reverse primer 5'-GGACATCTAAGGGCATCAC-3' (SEQ. ID. No. 28). PCR conditions were 95° C., 3 min, and 40 cycles of 95° C., 10 sec; 63.5° C., 45 sec. Specificity of PCR products were confirmed by gel electrophoresis.

Statistical analysis—Data are expressed as means±SEM. Unpaired Student's t-test and one-way repeated ANOVA measures including the Bonferroni test for all subgroups were performed for statistical comparisons when appropriate. For dose response curves ANOVA for repeated measures was used. For all tests, a value of $P<0.05$ was accepted as statistically significant.

Results

Figure 6:
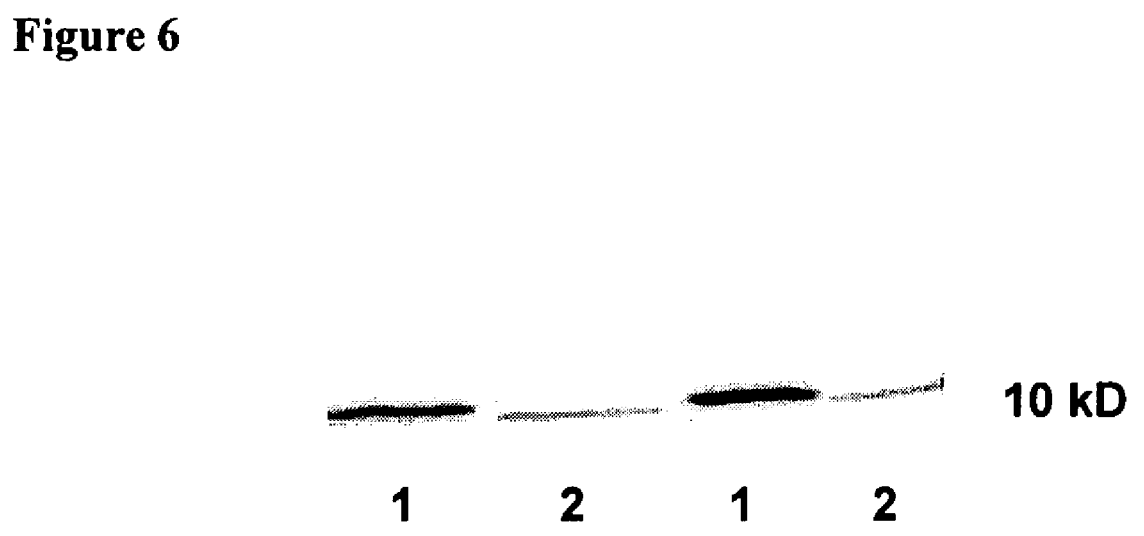

S100A1 is expressed in endothelial cells—Since S100A1 expression was recently described in rat cerebral endothelial cells,[43] experiment was undertaken to confirmed the expression of S100A1 in human coronary endothelial cells (HCAEC), rat cardiac endothelial cells (RCEC) and mouse aortic endothelial cells (MAEC). Indirect immunofluorescence staining for S100A1 was consistently observed in the perinuclear region accentuated at one pole of the nucleus (data not shown). Endogenous expression of S100A1 in EC could also be detected by western blotting (FIG. 6). Importantly, S100A1 was found in WT but not SKO derived MAEC in aortic vessel cryosections by immunohistochemistry (data not shown).

Figure 7:
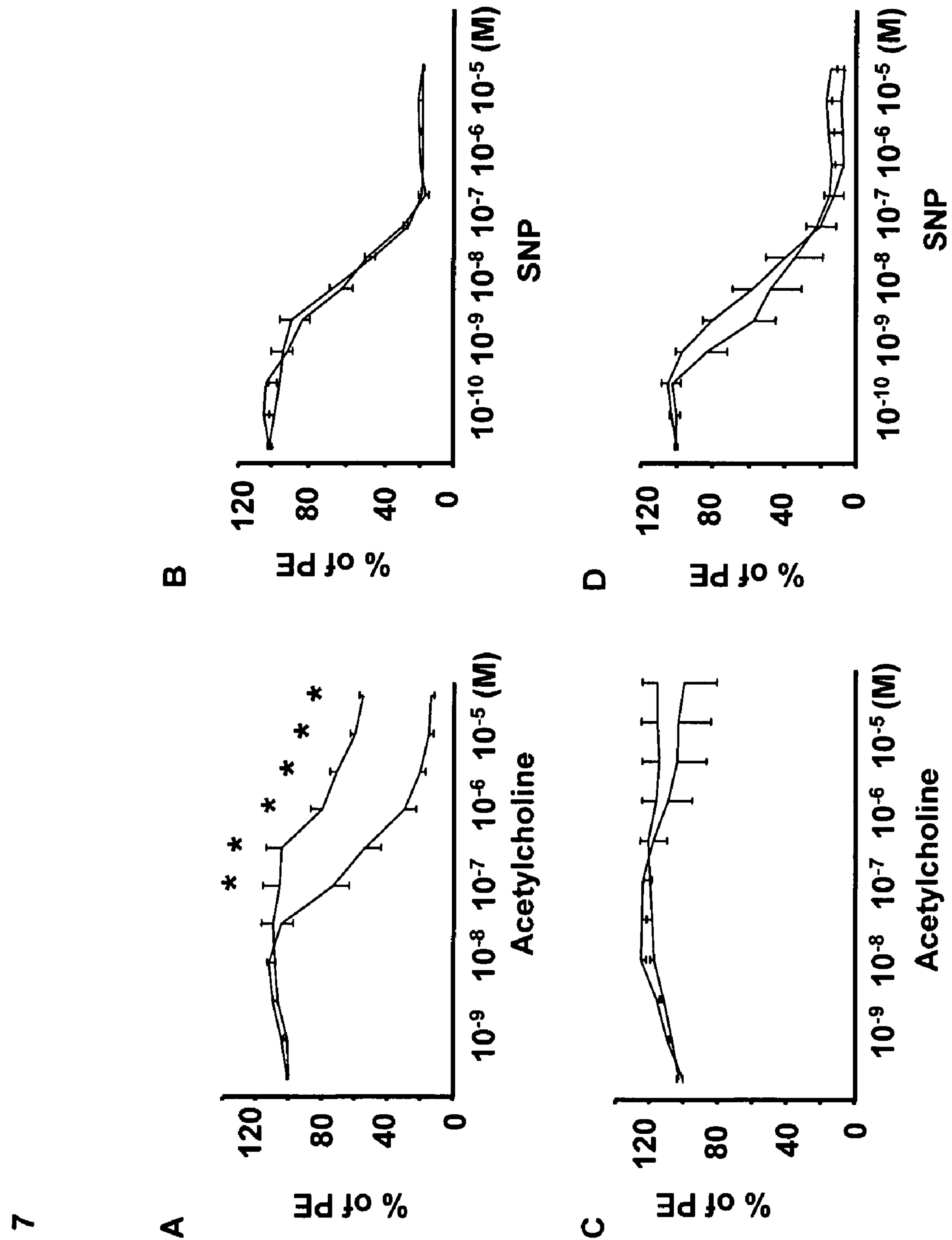
FIG. 7 Impaired endothelium-dependent vessel relaxation in aortas from SKO mice. (A) ACh-induced relaxation of PE-preconstricted (EC50) thoracic aortas was significantly reduced in SKO-derived aortas (black; n=6) compared to WT control aortas (grey; n=6). (B) Direct vessel relaxation of preconstricted aortas using SNP was not different between SKO (black; n=6) and WT groups (grey; n=6). Removal of EC resulted in similar responses of SKO and WT-derived aortas to (C) ACh or (D) SNP. P<0.05.

Expression of S100A1 in EC is pivotal for endothelium-dependent vessel relaxation—SKO mice were used to investigate the role of endogenous S100A1 in EC.[11] The effect of S100A1 expression independent of autonomic influences on the vasculature was examined in isolated thoracic aorta rings. PE-mediated constriction of aortic rings from both the WT and SKO mice were similar. Pre-tension was established using an $EC_{50}$ dose of $3\times10^{7}$M PE. Interestingly, endothelium-dependent relaxation in response to increasing concentrations of acetylcholine (ACh) was significantly impaired in thoracic aortas from SKO (n=6) compared to WT (n=6). Moreover, the maximal response to ACh was significantly attenuated in SKO aortas compared to WT controls (55±6.49% vs. 14±2.41% of PE-precontraction; $p<0.05$) and the agonist-induced response curve was shifted to the right in SKO (FIG. 7A). To verify endothelium-dependence of the reduced relaxation in response to ACh and to rule out an inability of the smooth muscle cells to respond to NO, relaxation was induced by the direct NO donor SNP. No significant difference in direct SNP-induced vessel relaxation was observed between SKO and WT (FIG. 7B). Importantly, mechanical scraping of EC resulted in similar vessel reactivity in SKO (n=6) or WT (n=6) mice in response to SNP, ACh (FIGS. 7C and 7D) or PE (data not shown).

Figure 8:
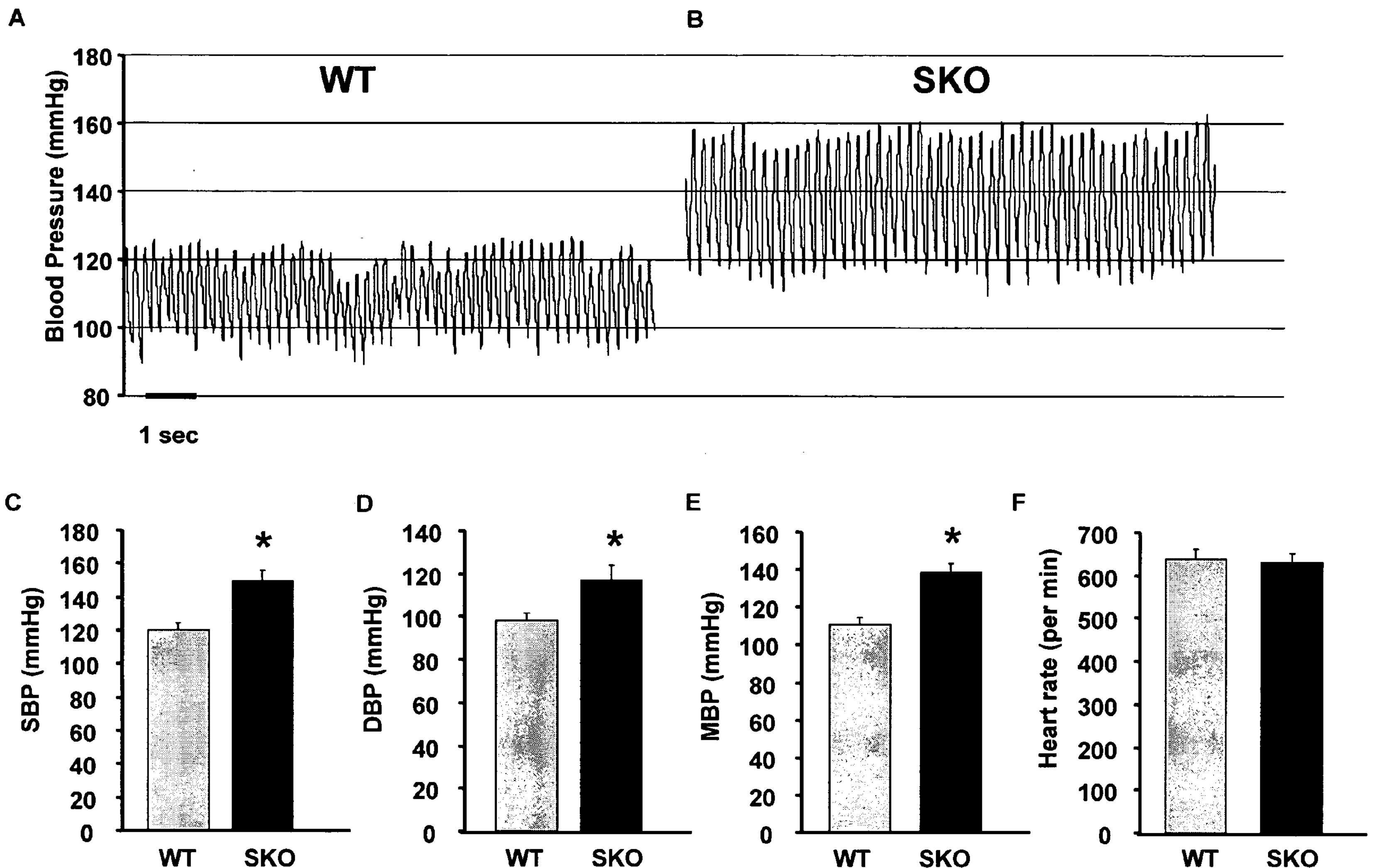
FIG. 8 Endothelial dysfunction is associated with increased blood pressure in vivo. Representative raw traces of (A) WT and (B) SKO mice. (C) Systolic blood pressure (SBP), (D) diastolic blood pressure (DBP) and (E) mean arterial blood pressure (MBP) were significantly increased in SKO mice (n=7) in vivo compared to WT controls (n=6) while (F) heart rate was similar in both groups. * P<0.05. Data is presented as mean±SEM.

Endothelial dysfunction in SKO is associated with hypertension—Since the lack of S100A1 expression in EC translates into endothelial dysfunction and a deficit in vascular relaxation in vitro, the impact of S100A1 expression on blood pressure in vivo was determined. Interestingly, conscious SKO mice (n=7) which exhibit endothelial dysfunction showed, a significant 24% increase in systolic blood pressure (SBP) in vivo compared to conscious WT mice (n=6) (FIG. 8A). Moreover, mean arterial blood pressure (MAP) and diastolic blood pressure (DBP) were also significantly elevated in SKO compared to WT while the heart rate was unaltered (FIGS. 8B-D). Therefore, loss of S100A1 is associated with hypertension in vivo and S100A1 expression in EC might contribute to regulating and maintaining normal blood pressure.

Figure 9:
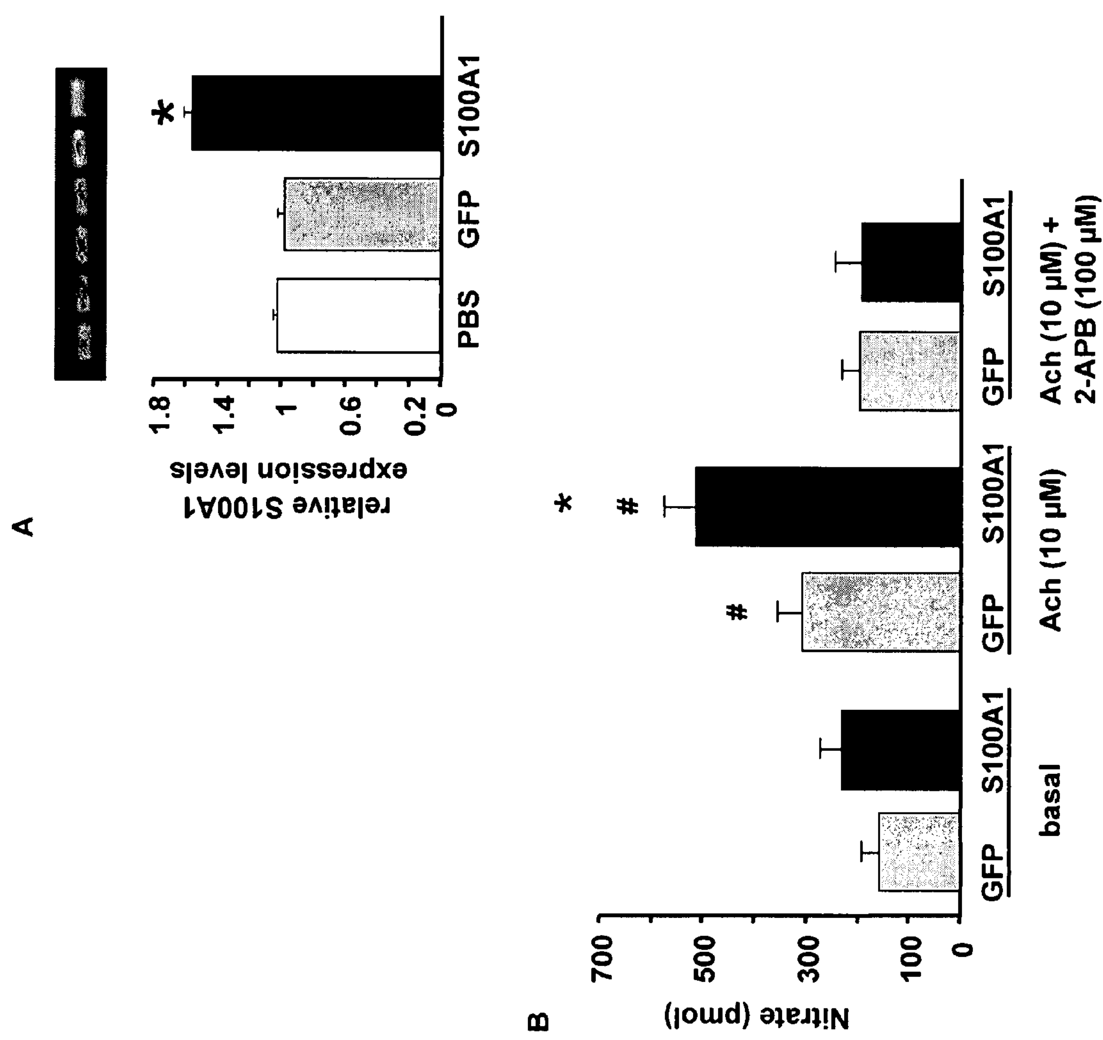
FIG. 9 S100A1 over-expression increases agonist-induced NO generation in HCAEC. Transfection of the plasmid pAdTrack-S100A1 in HCAEC was controlled by GFP co-expression. Transfection of the plasmid pAdTrack-GFP resulted in similar GFP expression (data not shown). (A) RT-PCR reveals a 1.6 fold increase in S100A1 expression in HCAEC due to pAdTrack-S100A1 transfection compared to both PBS and GFP control groups. (B) Basal NO generation, as measured by the stable end product nitrate, was unaltered in all groups after 1 hour in cultured HCAEC. GFP and S100A1 groups showed a significant agonist-induced increase in NO generation. S100A1 over-expression significantly increased ACh-induced NO generation compared to GFP controls groups. Blockage of IP3R-mediated Ca2+-release (by use of 2-APB) significantly reduced ACh-stimulated NO production and masked S100A1 mediated effects. * P<0.05; S100A1/ACh vs. GFP/ACh. # P<0.05; GFP/ACh vs. GFP/basal or S100A1/ACh vs. S100A1/basal. Data is presented as mean±SEM.

S100A1 affects agonist-induced NO generation in HCAEC—ACh-induced vascular relaxation is largely mediated via endothelial NO and NO levels affect vascular tone contributing to blood pressure regulation and vascular function.[47] Accordingly, whether an increased S100A1 expression in EC will stimulate NO generation was tested. Additionally, since S100A1 stimulates $[Ca^{2+}]_i$-cycling in various cell types and the Ach-induced increase in NO is mainly mediated via increased $[Ca^{2+}]_i$, the impact of the blockage of the $IP_3R$ on the S100A1-mediated increase in NO generation was studied. Transfection of the plasmid pAdTrack-S100A1 yielded ~50% GFP positive HCAEC and a 1.6-fold overexpression of S100A1 compared to GFP and PBS control groups (FIG. 9A). Under all conditions tested there were no significant differences in NO production between the PBS and GFP groups. ACh significantly increased NO generation in all groups (FIG. 9B). Importantly, ACh-induced NO generation was significantly increased in S100A1 overexpressing HCAEC compared to control groups (FIG. 9B). Consistently, blockage of the $IP_3R$ agonist-induced $[Ca^{2+}]_i$-transients by use of 2-APB abolished NO generation in all groups and masked the difference between S100A1 and control groups (FIG. 9B). Thus, S100A1 overexpression enhances endothelial NO generation and this effect is, at least in part, $[Ca^{2+}]_i$-dependent.

Figure 10:
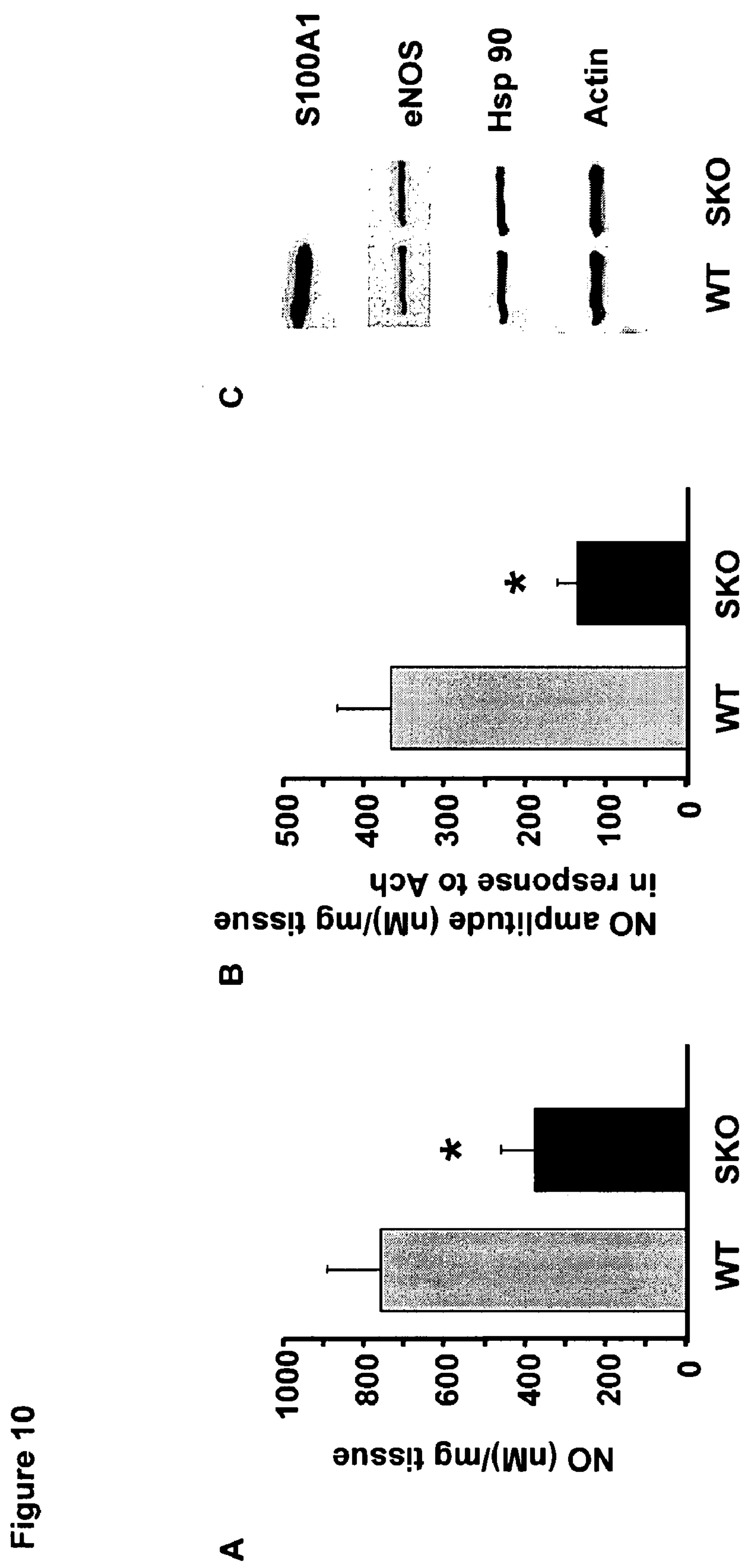
FIG. 10 Endothelial S100A1 modulates basal and agonist-induced NO generation. NO production was measured at the endothelial surface of thoracic aortas and found to be significantly reduced in SKO aortas (n=4) compared to WT aortas (n=4) both under basal conditions (A) as well as under ACh (10-5 M) stimulation (B). (C) Depicts representative western blots for S100A1, eNOS, Hsp90 and actin in SKO and WT mice. * P<0.05. Data is presented as mean±SEM.

Endogenous S100A1 is critical for aortic NO release—It was demonstrated that S100A1 overexpression in HCAEC increases agonist-induced endothelial NO generation in a $Ca^{2+}$-dependent manner. To investigate the functional role of endogenous S100A1 in EC and to gain mechanistic insight into endothelial dysfunction and impaired vascular relaxation observed in SKO thoracic aorta, real-time levels of aortic endothelial NO release in SKO and WT mice were measured. Interestingly, basal aortic NO levels were significantly reduced by ~50% in SKO (n=4) compared to WT (n=4) mice (FIG. 10A). Additionally, the ACh ($10^{-5}$ M) stimulated increase in aortic endothelial NO release was significantly blunted due to the lack of endogenous S100A1 in vascular tissue (368.2±68.1 vs. 134.5±25.3 nM NO/mg tissue; $p<0.05$, FIG. 10B). Thus, loss of endogenous S100A1 expression in EC leads to a significant reduction of both basal and ACh-induced NO levels. Importantly, equal expression of eNOS and its critical regulator Hsp90 in WT and SKO mice was confirmed by western blotting in lung tissue as well as in skeletal muscle and lack of S100A1 expression was confirmed in SKO mice by western blot for S100A1 in cardiac tissue (FIG. 10C).

Figure 11:
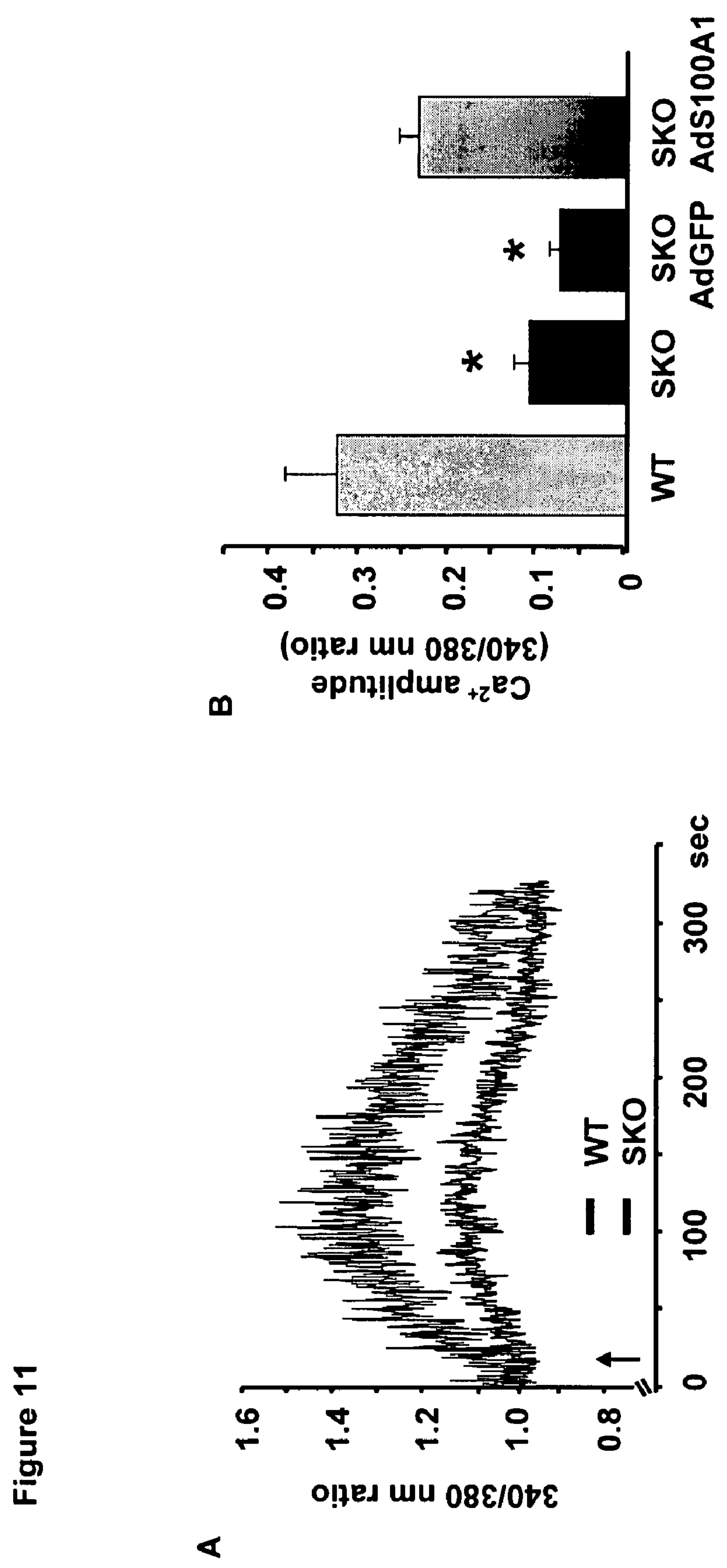
FIG. 11 Lack of S100A1 expression in EC causes reduced ACh-induced [Ca2+]i-transients. (A) Representative raw traces of ACh-induced [Ca2+]i-transients in MAEC from WT mice (grey) and SKO mice (black). (B) [Ca2+]i-transients in response to ACh stimulation were significantly decreased in MAEC from SKO mice (n=15) compared to WT MAEC (n=15). Adenoviral expression of S100A1 (AdS100A1) significantly increased ACh-induced [Ca2+]i-transients in SKO-derived MAEC (n=15) while an AdGFP control virus did not affect [Ca2+]i-transients (n=13). * P<0.05 compared to WT or SKO/AdS100A1. Data is presented as mean±SEM.

Endothelial S100A1 modulates ACh-induced $Ca^{2+}$-transients—Classically, eNOS activation is dependent on an increase in $[Ca^{2+}]_i$ and the binding of $Ca^{2+}$/Calmodulin to the enzyme, while chelation of extracellular $Ca^{2+}$ abolishes agonist-induced NO generation and vascular relaxation.[46] In cardiomyocytes, S100A1 is known to mechanistically act via a significant gain in $[Ca^{2+}]_i$.[10,13] Importantly, it was found that S100A1 mediated increase in NO production in HCAEC was masked upon $IP_3R$-blockage. Therefore, the impact of S100A1 on ACh-induced $[Ca^{2+}]_i$ in EC was investigated. SKO-derived EC (n=15) showed a significantly reduced $[Ca^{2+}]_i$ response to ACh as compared to WT (n=15) (FIG. 11). To insure that the observed effects were due to the lack of S100A1 expression in SKO, S100A1 was expressed in SKO using an adenoviral construct (AdS100A1). AdGFP was used as a control and infection of EC with both vectors were confirmed by GFP co-expression. Interestingly, S100A1 expression in SKO-EC (n=15) significantly increased ACh-induced $[Ca^{2+}]_i$ compared to SKO-EC treated with the control virus (n=13) (FIG. 11A). Endothelial S100A1 expression might therefore be essential for adequate $[Ca^{2+}]_i$-transients in response to agonists.

S100A1 co-localizes with both the $IP_3$-receptor and SERCA2—To further investigate the underlying mechanism of reduced $[Ca^{2+}]_i$-transients in SKO-EC and to identify potential target proteins for S100A1 in EC, the localization of S100A1, the SERCA2 and the $IP_3$-R was studied. Endogenous S100A1 is mainly localized to areas where SERCA2 and $IP\text{-}_3R$ are found (Data not shown).

Figure 12:
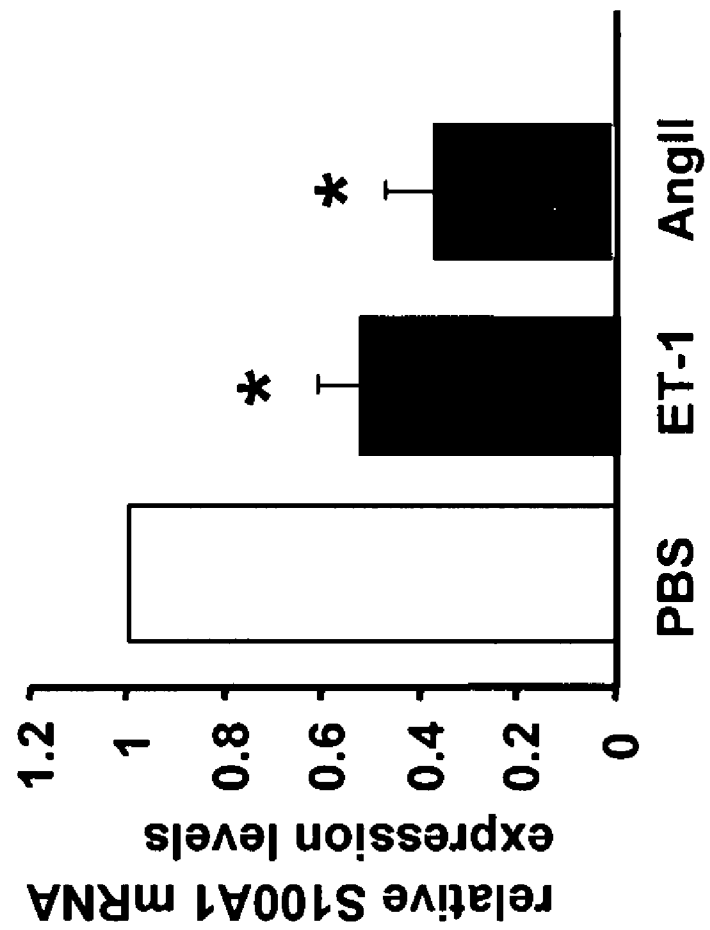
FIG. 12 Endothelin-1 (ET-1) or angiotensin II (Ang II) (both 10-7 M) significantly reduce S100A1 mRNA expression in RCEC after 60 hours. Experiments were done in triplicate; 3 individual experiments. * P<0.05 vs. PBS. Data is presented as mean±SEM.

Angiotensin II and endothelin-1 stimulation decrease S100A1 expression in EC—To investigate whether reduced S100A1 expression in EC could potentially be involved in endothelial dysfunction in cardiovascular diseases, HCAEC and RCEC were stimulated with angiotensin II (Ang II) or endothelin-1 (ET-1) both known to be increased in a variety of cardiovascular diseases and involved in cardiac and vascular remodelling.[55,56] Ang II and ET-1 stimulation (both $10^{-7}$ M) significantly reduced S100A1 mRNA levels after 60 hours in vitro (FIG. 12).

The EF-hand-type $Ca^{2+}$ sensing protein S100A1 plays a significant role in cardiovascular function since it has been characterized as a novel positive inotropic factor and regulator of myocardial contractility in vitro and in vivo.[7,6,9] Moreover, S100A1 gene therapy has been shown to rescue HF and to preserve cardiac function after acute myocardial infarction in animal models in vivo, mainly by causing a significant gain in $[Ca^{2+}]_i$-cycling in cardiomyocytes.[13,15] Importantly, vascular function and one of its major regulators, eNOS, are also critically regulated by $[Ca^{2+}]_i$.[44-46] An increase in $[Ca^{2+}]_i$ activates Calmodulin (CaM) which displaces an autoinhibitory loop and binds to eNOS facilitating NADPH-dependent electron flux from the reductase domain of the protein to the oxygenase domain.[13] Loss of endothelial NO causes endothelial dysfunction which is linked to a large number of cardiovascular diseases and was shown to be associated with an increased mortality risk in patients with both ischemic and non-ischemic HF.[48-49] Since S100A1 was recently reported to be expressed in EC, and given the relevance of EC in cardiovascular diseases, the impact of S100A1 in the vascular function was investigated. It was found that a loss of S100A1 is critical in EC, resulting in vascular dysfunction and hypertension.

Specifically, it was demonstrated that there is a critical role for endothelial S100A1 in vascular function since endothelium-dependent relaxation of SKO thoracic aortas was significantly reduced compared to WT. Direct vessel relaxation using SNP was not different between both groups revealing that smooth muscle cells also lacking S100A1 expression in SKO mice relax normally in response to NO. To address a potential relevance of the impaired vascular function under in vivo conditions, blood pressure in conscious SKO and WT mice was measured. Both, systolic and diastolic blood pressure was significantly higher in SKO mice. Therefore, the data indicates that endothelial dysfunction due to the lack of S100A1 expression in EC can contribute to vascular dysfunction in vivo and that endothelial S100A1 can be critical for the maintenance of normal blood pressure. Mechanistically, both, basal and ACh-induced NO release analyzed directly at the endothelial surface of aorta were significantly decreased in SKO-thoracic aorta compared to WT controls. The data indicates that diminished $[Ca^{2+}]_i$-transients in S100A1 lacking EC contribute to reduced eNOS activation, and thus, NO generation in SKO mice. Importantly, adenoviral mediated expression of S100A1 in MAEC from SKO mice resulted in restoration of $[Ca^{2+}]_i$-transients demonstrating that the observed effects were specifically mediated by the S100A1 protein.

S100A1 enhances $[Ca^{2+}]_i$-cycling in cardiomyocytes by an increase in SERCA2a activity and a biphasic modulation of the open probability of the ryanodine receptor (RyR).[8,13,14] Co-immunofluorescence revealed co-localization for S100A1 with both SERCA and $IP_3R$ in the perinuclear region also in EC. Therefore, SERCA and the $IP_3R$ might be potential target proteins for S100A1 in EC and modulation of SERCA or $IP_3R$ activity might further be involved in altered endothelial $[Ca^{2+}]_i$-transients. Notably, the SERCA3 knockout mouse shows a phenotype of decreased ACh-induced $[Ca^{2+}]_i$-transients and impaired endothelium-dependent vessel relaxation similar to our results but lacks the development of high blood pressure.[57] Moreover, the agonist-induced increased NO production in S100A1 overexpressing HCAEC was blocked by the use of the $IP_3R$ blocker 2-APB demonstrating that the S100A1 mediated effect is, at least in part, $[Ca^{2+}]_i$-dependent.

Noteworthy, various transduction pathways mediated by extracellular signals can modulate eNOS activity. Intrinsic control of eNOS function such as myristoylation and post-translational cysteine palmitoylation or eNOS associated proteins also control subcellular targeting and the activation state of the enzyme, and thus NO generation.[44-47] Importantly, eNOS protein expression as well as expression of Hsp90, a molecular chaperone, known to interact with S100A1 and to regulate eNOS activity,[58-59] was not altered in EC from SKO mice compared to WT.

Cardiac S100A1 protein expression is known to be down-regulated in HF in vivo and $G_q$-protein receptor agonists reduce S100A1 expression in cardiomyocytes in vitro.[12,16] Since endothelial dysfunction is a characteristic of a variety of cardiovascular diseases and risk factors such as hypertension, HF, chronic smoking and hypercholesterolemia,[48,49,55] the impact of neurohumoral stimulation involved in vascular and cardiac remodeling were investigated. Decreased S100A1 expression following ET-1 and Ang II stimulation in vitro indicates that reduced endothelial S100A1 levels could potentially be implicated in the development of endothelial dysfunction in cardiovascular diseases.[55] Since S100A1 overexpression in HCAEC caused a significant increase in ACh-induced NO generation, in vivo increasing/normalizing endothelial S100A1 could potentially add to existing therapeutic strategies to treat cardiovascular diseases.

The study confirms S100A1 expression in EC and reports on a novel essential role for S100A1 in vascular function. Importantly, the critical nature of S100A1 in EC function was found both in vitro and in vivo and all data demonstrate that the loss of S100A1 causes endothelial dysfunction including hypertension. It was found that, endothelial S100A1 expression is essential for agonist-induced $[Ca^{2+}]_i$-transients and this can contribute to reduced eNOS activity and decreased NO generation in EC lacking S100A1 expression. Endothelial dysfunction in SKO mice translates into impaired endothelium-dependent vascular relaxation and increased systolic and diastolic blood pressure in vivo. Finally, S100A1 is down-regulated upon neurohumoral stimulation involved in vascular and cardiac remodelling. Therefore, S100A1 in EC plays a critical role for vascular function and targeting endothelial S100A1 expression might be a novel therapeutic means to improve endothelial function in vascular disease or HF.

The references disclosed herein are hereby incorporated by reference in their entirety.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

References

1. American Heart Association. (2005). Heart Disease and Stroke Statistics. www.americanheart.org
2. Cohn, J. N. et al. Report of the National Heart, Lung, and Blood Institute Special Emphasis Panel on Heart Failure Research. Circulation. 95, 766-770 (1997).
3. Rich, M. W. Epidemiology, pathophysiology, and etiology of congestive heart failure in older adults. J. Amer. Geriatr. Soc. 45, 968-974 (1997).
4. del Monte F, Hajjar R. Targeting calium cycling proteins in heart failure through gene transfer. J. Physiol. 546, 49-61 (2003).
5. Wehrens X H, Marks A R. Novel therapeutic approaches for heart failure by normalizing calcium cycling. Nat. Rev. Drug. Discov. 3, 565-573 (2004).
6. Most, P. et al. S100A1: a regulator of myocardial contractility. Proc. Natl. Acad. Sci. USA. 98, 13889-13894 (2001).
7. Most, P. et al. Transgenic overexpression of the Ca2+ binding protein S100A1 in the heart leads to increased in vivo myocardial contractile performance. J. Biol. Chem. 278, 33809-33817 (2003).
8. Most, P. et al. Distinct subcellular location of the Ca2+ binding protein S100A1 differentially modulates Ca2+ cycling in ventricular rat cardiomyocytes. J. Cell Science 118, 421-431 (2005).
9. Remppis, A. et al. S100A1 gene transfer: a strategy to strengthen engineered cardiac grafts. J. Gene Med. 6, 387-394 (2004).
10. Remppis, A. et al. The small EF-hand Ca2+ binding protein S100A1 increases contractility and Ca2+ cycling in rat cardiac myocytes. Basic Res. Cardiol. 97, I56-I62 (2002).
11. Du, X. J. et al. Impaired cardiac contractility response to hemodynamic stress in S100A1-deficient mice. Mol. Cell. Biol. 22, 2821-2829 (2002).
12. Most P., et al. Cardiac S100A1 protein levels determine contractile performance and propensity towards heart failure after myocardial infarction. Circulation 114(12):1258-68 (2006).
13. Most, P. et al. Cardiac adenoviral S100A1 gene delivery rescues failing myocardium. J. Clin. Invest. 114, 1550-1563 (2004).
14. Kettlewell, S., Most, P., Currie, S., Koch, W. J., Smith, G. L. S100A1 increases the gain of excitation-contraction coupling in isolated rabbit ventricular cardiomyocytes. J. Mol. Cell. Cardiol 39, 900-910 (2005).
15. Pleger, S. T., et al. S100A1 gene therapy preserves in vivo cardiac function after myocardial infarction. Mol Ther. 12, 1120-1129 (2005).
16. Remppis, A., et al. Altered expression of the Ca2+-binding protein S100A1 in human cardiomyopathy. Biochim. Biophys. Acta 1313, 253-257 (1996).
17. Williams M L, Koch W J: Viral-based myocardial gene therapy approaches to alter cardiac function. Annu. Rev. Physiol. 66, 49-75 (2004).
18. Eichhorn E. J. Restoring function in failing hearts: the effects of beta blockers. Am. J. Med. 104, 163-169 (1998).
19. Katz A. Potential deleterious effects of inotropic agents in the therapy of chronic heart failure. Circulation 73, III184-III190 (1986).
20. Mukherjee, R., et al. Myocardial infarct expansion and matrix metalloproteinase inhibition. Circulation. 107, 618-625 (2003).
21. Ciulla M. M., et al. Left ventricular remodeling after experimental myocardial cryoinjury in rats. J. Surg. Res. 116, 91-97 (2004).
22. Lemonnier, M., Buckingham, M. Characterization of a cardiac-specific enhancer, which directs α-cardiac actin gene transcription in the mouse adult heart. J. Biol. Chem. 279, 55651-55658 (2004).
23. Katz A. M. Proliferative signaling and disease progression in heart failure. Circ J. 66(3):225-31 (2002).
24. Esler M. Measurement of sympathetic nervous system activity in heart failure: the role of norepinephrine kinetics. Heart Fail Rev. 5(1):17-25 (2000).
25. Sabbah H. N., Sharov V. G., Goldstein S. Cell death, tissue hypoxia and the progression of heart failure. Heart Fail Rev. 5(2):131-8 (2000).
26. Tsoporis, J. N., Marks, A., Zimmer, D. B., McMahon, C., Parker, T. G. The myocardial protein S100A1 plays a role in the maintenance of normal gene expression in the adult heart. Mol. Cell Biochem. 242: 27-33 (2003).
27. Omerovic E., Bollano E., Soussi B., Waagstein F. Selective beta1-blockade attenuates post-infarct remodelling without improvement in myocardial energy metabolism and function in rats with heart failure. Eur J Heart Fail. 5(6):725-32 (2003).

28. Yang Y., et al. Comparison of metoprolol with low, middle and high doses of carvedilol in prevention of postinfarction left ventricular remodelling in rats. Jpn Heart J. 44(6):979-88 (2003).

29. Ahmet I., et al. Beneficial effects of chronic pharmacological manipulation of beta-adrenoreceptor subtype signaling in rodent dilated ischemic cardiomyopathy. Circulation. 110; 1083-1090 (2004).

30. Janosi A., et al. Metoprolol CR/XL in postmyocardial infarction patients with chronic heart failure: experiences from MERIT-HF. Am Heart J. 146(4):721-8 (2003).

31. Williams R. E. Early initiation of beta blockade in heart failure: issues and evidence. Clin Hypertens. 7(9):520-8 (2005).

32. Engelhardt, S., Hein, L., Wiesmann, F., Lohse, M. J. Progressive hypertrophy and heart failure in β1-adrenergic receptor transgenic mice. Proc. Natl. Acad. Sci. USA. 96, 7059-7064 (1999).

33. Volkers M., et al. S100A1 decreases calcium spark frequency and alters their characteristics in permeabilized adult ventricular cardiomyocytes. Cell Calcium; in press (2006).

34. Chen Y., et al. Constitutive cardiac overexpression of sarcoplasmic/endoplasmic reticulum Ca2+-ATPase delays myocardial failure after myocardial infarction in rats at a cost of increased acute arrhythmias. Circulation. 20; 109 (15):1898-903 (2004).

35. Haberman, R., Lux, G., McGown, T., Samulski R. J. Production of recombinant adeno-associated viral vectors and use in in vitro and in vivo administration, p. 4.17.1-4.17.25. In J. Crawley, C. Gerfen, M. Rogawski, L. Sibley, P. Skolnick, and S. Wray (ed.), Current protocols in neuroscience, Vol 1. John Wiley & Sons, Inc., New York, N.Y. (1999).

36. Xiao, X., Li, J., Samulski, R. Production of high titer recombinant adeno-associated virus vectors in the absence of helper adenovirus. J. Virol. 72: 2224-2232 (1998).

37. Rabinowitz, J. E., Rolling, F., Li, C., Conrath, H., Xiao, W., Xiao, X., Samulski R. J. Cross-packaging of single adeno-associated virus (AAV) type 2 vector genome into multiple AAV serotypes enables transduction with broad specificity. J. Virol. 76: 791-801 (2002).

38. Zimmer D B, Chaplin J, Baldwin A, Rast M. S100-mediated signal transduction in the nervous system and neurological diseases. *Cell Mol Biol* (*Noisy-le-grand*). 2005; 5; 51(2):201-14.

39. Fano G, Marsili V, Angelella P, Aisa M C, Giambanco I, Donato R. S-100a0 protein stimulates Ca2+-induced Ca2+ release from isolated sarcoplasmic reticulum vesicles. *FEBS Lett.* 1989; 25; 255(2):381-4.

40. Donato R. Functional roles of S100 proteins, calcium-binding proteins of the EF-hand type. *Biochim Biophys Acta.* 1999; 8; 1450(3):191-231.

41. Schafer B W, Heizmann C W. The 5100 family of EF-hand calcium-binding proteins: functions and pathology. *Trends Biochem Sci.* 1996; 21(4):134-40.

42. Zimmer D B, Cornwall E H, Landar A, Song W. The S100 protein family: history, function, and expression. *Brain Res Bull.* 1995; 37(4):417-29.

43. Lefranc F, Decaestecker C, Brotchi J, Heizmann C W, Dewitte O, Kiss R, Mijatovic T. Co-expression/co-location of S100 proteins (S 100B, S100A1 and S100A2) and protein kinase C (PKC-beta, -eta and -zeta) in a rat model of cerebral basilar artery vasospasm. *Neuropathol Appl Neurobiol.* 2005; 31(6):649-60.

44. Nathan C, Xie Q W. Nitric oxide synthases: roles, tolls, and controls. *Cell.* 1994; 23; 78(6):915-8.

45. Sessa W C. eNOS at a glance. *Cell Sci.* 2004; 15; 117(Pt 12):2427-9.

46. Fleming I, Busse R. Molecular mechanisms involved in the regulation of the endothelial nitric oxide synthase. *Am J Physiol Regul Integr Comp Physiol.* 2003; 284(1):R1-12.

47. Moncada S, Palmer R M, Higgs E A. Nitric oxide: physiology, pathophysiology, and pharmacology. *Pharmacol Rev.* 1991; 43(2):109-42.

48. Drexler H, Hornig B. Endothelial dysfunction in human disease. *J Mol Cell Cardiol.* 1999; 31(1):51-60.

49. Katz S D, Hryniewicz K, Hriljac I, Balidemaj K, Dimayuga C, Hudaihed A, Yasskiy A. Vascular endothelial dysfunction and mortality risk in patients with chronic heart failure. *Circulation.* 2005; 25; 111(3):310-4.

50. Iaccarino G, Ciccarelli M, Sorriento D, Cipolletta E, Cerullo V, Iovino G L, Paudice A, Elia A, Santulli G, Campanile A, Arcucci O, Pastore L, Salvatore F, Condorelli G, Trimarco B. AKT participates in endothelial dysfunction in hypertension. Circulation. 2004; 1; 109(21):2587-93.

51. Marelli-Berg F M, Peek E, Lidington E A, Stauss H J, Lechler R I. Isolation of endothelial cells from murine tissue. *J Immunol Methods.* 2000; 20; 244(1-2):205-15.

52. Stalker T J, Gong Y, Scalia R. The calcium-dependent protease calpain causes endothelial dysfunction in type 2 diabetes. *Diabetes.* 2005; 54(4):1132-40.

53. Eckhart A D, Ozaki T, Tevaearai H, Rodman H A, Koch W J. Vascular-targeted overexpression of G protein-coupled receptor kinase-2 in transgenic mice attenuates βadrenergic receptor signaling and increases resting blood pressure. *Mol Pharmacol.* 2002; 61: 749-758.

54. He T C, Zhou S, da Costa L T, Yu J, Kinzler K W, Vogelstein B. A simplified system for generating recombinant adenoviruses. *Proc Natl Acad Sci USA.* 1998; 3; 95(5): 2509-14.

55. Touyz R M. Intracellular mechanisms involved in vascular remodelling of resistance arteries in hypertension: role of angiotensin II. *Exp Physiol.* 2005; 90(4):449-55.

56. Fleming I, Kohlstedt K, Busse R. The tissue renin-angiotensin system and intracellular signalling. *Curr Opin Nephrol Hypertens.* 2006; 15(1):8-13.

57. Liu L H, Paul R J, Sutliff R L, Miller M L, Lorenz J N, Pun R Y, Duffy J J, Doetschman T, Kimura Y, MacLennan D H, Hoying J B, Shull G E. Defective endothelium-dependent relaxation of vascular smooth muscle and endothelial cell Ca2+ signaling in mice lacking sarco(endo)plasmic reticulum Ca2+-ATPase isoform 3. *J Biol Chem.* 1997; 28; 272 (48):30538-45.

58. Garcia-Cardena G, Fan R, Shah V, Sorrentino R, Cirino G, Papapetropoulos A, Sessa W C. Dynamic activation of endothelial nitric oxide synthase by Hsp90. *Nature.* 1998; 23; 392(6678):821-4.

59. Okada M, Hatakeyama T, Itoh H, Tokuta N, Tokumitsu H, Kobayashi R. S100A1 is a novel molecular chaperone and a member of the Hsp70/Hsp90multichaperone complex. *J Biol Chem.* 2004 Feb. 6; 279(6):4221-33.

What is claimed:

1. A cardiac tissue-specific nucleic acid segment comprising:

(a) a first regulatory sequence comprising;
a cardiac specific enhancer sequence comprising two myocyte-enhancer factor-2 (MEF2) sequences, and two enhancer MyoD consensus sequences of the proximal enhancer region of an α cardiac actin gene, (b) a second regulatory sequence comprising a promoter sequence; and (c) a multiple restriction site for insertion of a target nucleic acid operatively linked to the second regulatory sequence.

2. The cardiac tissue-specific nucleic acid segment of claim 1, wherein the cardiac specific enhancer sequence further comprises a repressor sequence.

3. The cardiac tissue-specific nucleic acid segment of claim 1, wherein the promoter sequence comprises an EF1 α promoter sequence.

4. A gene delivery vector comprising the cardiac tissue-specific nucleic acid segment of claim 1.

5. The gene delivery vector of claim 4, wherein the vector is selected from the group consisting of an adeno-associated virus, an adenovirus, a lentivirus, a retrovirus, and naked DNA.

6. A cardiac tissue-specific nucleic acid segment comprising:

(a) a first regulatory sequence comprising a cardiac specific enhancer sequence comprising the sequence AGGAAT- TCTAAATTTACGTCTGCTTCCTGT- CAATGGGCATCCTCACTGTCA AATGCAGATGG- TACAGCAGGGCTTGGTCTCAGCCAGGCA GGCCTCTCCCC AGTCTCCATGGCTCAGCTGTC- CAGCAGTTTCATCCCTAGACCATCCCAAAC ATGGTTGAGAAGCTCTGAGGGGAGGAC- CCAGCACTGCCCGGCCCCTGAAG TATCTAAT- CAGCAGTCCTGCTCAGCATATCAATC- CAAGCCCACTCTAGACA GAGATGCCGGTGCCCAGTTTTCTATTTT- TAACTGGTGTGAACTGAAGGAAA AAGCAGCT- GACTAGT (SEQ. ID. No. 1) and one or two myocyte-enhancer factor-2 (Mef2) sequences CTA(A/T)4TAG (SEQ. ID. No. 3 or 4);

(b) a second regulatory sequence comprising a promoter sequence; and (c) a multiple restriction site for insertion of a target nucleic acid operatively linked to the second regulatory sequence.

7. The cardiac tissue-specific nucleic acid segment of claim 1 further comprising a target nucleic acid inserted within the multiple restriction site and is operatively linked to the second regulatory sequence.

8. The cardiac tissue-specific nucleic acid segment of claim 7, wherein the target nucleic acid is selected from the group consisting of S100A1, SERCA, FK506BP 12.6, phospholamban, inhibitory RNAs for NKX, GRK2, GRK5, and the carboxyl terminal fragment of GRK2 (βARKct).

9. The cardiac tissue-specific nucleic acid segment of claim 8, wherein the target nucleic acid is S100A1.

10. The cardiac tissue-specific nucleic acid segment of claim 6, wherein the cardiac specific enhancer sequence further comprises a repressor sequence.

11. The cardiac tissue-specific nucleic acid segment of claim 6, wherein the promoter sequence comprises an EF1 α promoter sequence.

12. A gene delivery vector comprising the cardiac tissue-specific nucleic acid segment of claim 6.

13. The gene delivery vector of claim 12, wherein the vector is selected from the group consisting of an adeno-associated virus, an adenovirus, a lentivirus, a retrovirus, and naked DNA.

14. The cardiac tissue-specific nucleic acid segment of claim 6 further comprising a target nucleic acid inserted within the multiple restriction site and is operatively linked to the second regulatory sequence.

15. The cardiac tissue-specific nucleic acid segment of claim 14, wherein the target nucleic acid is selected from the group consisting of S100A1, SERCA, FK506BP 12.6, phospholamban, inhibitory RNAs for NKX, GRK2, GRK5, and the carboxyl terminal fragment of GRK2 (βARKct).

16. The cardiac tissue-specific nucleic acid segment of claim 15, wherein the target nucleic acid is S100A1.

17. A liposome comprising the gene delivery vector of claim 4.

18. A liposome comprising the gene delivery vector of claim 12.

* * * * *

UNITED STATES PATENT AND TRADEMARK OFFICE

CERTIFICATE OF CORRECTION

PATENT NO. : 8,383,601 B2
APPLICATION NO. : 12/447558
DATED : February 26, 2013
INVENTOR(S) : Koch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 518 days.

Signed and Sealed this
First Day of September, 2015

Michelle K. Lee
*Director of the United States Patent and Trademark Office*